US009527852B2

(12) United States Patent
Wrasidlo

(10) Patent No.: US 9,527,852 B2
(45) Date of Patent: Dec. 27, 2016

(54) PHENYL-UREA AND PHENYL-CARBAMATE DERIVATIVES AS INHIBITORS OF PROTEIN AGGREGATION

(71) Applicant: Neuropore Therapies, Inc., San Diego, CA (US)

(72) Inventor: Wolfgang Wrasidlo, San Diego, CA (US)

(73) Assignee: NEUROPORE THERAPIES, INC., San Diego, CA (US)

( * ) Notice: Subject to any disclaimer, the term of this patent is extended or adjusted under 35 U.S.C. 154(b) by 0 days.

(21) Appl. No.: 14/388,783

(22) PCT Filed: Mar. 15, 2013

(86) PCT No.: PCT/US2013/032552
§ 371 (c)(1),
(2) Date: Sep. 26, 2014

(87) PCT Pub. No.: WO2013/148365
PCT Pub. Date: Oct. 3, 2013

(65) Prior Publication Data
US 2015/0166543 A1 Jun. 18, 2015

Related U.S. Application Data

(60) Provisional application No. 61/616,771, filed on Mar. 28, 2012.

(51) Int. Cl.
| | |
|---|---|
| *C07D 209/18* | (2006.01) |
| *C07D 235/16* | (2006.01) |
| *C07D 401/12* | (2006.01) |
| *C07D 403/12* | (2006.01) |
| *C07D 487/04* | (2006.01) |
| *A61K 31/4178* | (2006.01) |
| *A61K 31/404* | (2006.01) |
| *A61K 31/496* | (2006.01) |
| *A61K 31/4985* | (2006.01) |
| *C07D 235/06* | (2006.01) |
| *C07D 235/14* | (2006.01) |
| *C07D 471/04* | (2006.01) |
| *C07D 209/10* | (2006.01) |
| *C07D 209/12* | (2006.01) |
| *C07D 209/14* | (2006.01) |

(52) U.S. Cl.
CPC ......... *C07D 487/04* (2013.01); *C07D 209/10* (2013.01); *C07D 209/12* (2013.01); *C07D 209/14* (2013.01); *C07D 209/18* (2013.01); *C07D 235/06* (2013.01); *C07D 235/14* (2013.01); *C07D 401/12* (2013.01); *C07D 403/12* (2013.01); *C07D 471/04* (2013.01)

(58) Field of Classification Search
None
See application file for complete search history.

(56) References Cited

U.S. PATENT DOCUMENTS

| | | |
|---|---|---|
| 2003/0125354 A1 | 7/2003 | Hao et al. |
| 2004/0097499 A1 | 5/2004 | Arnold et al. |

FOREIGN PATENT DOCUMENTS

| | | |
|---|---|---|
| EP | 1 402 888 | 3/2004 |
| WO | WO-97/27192 | 7/1997 |
| WO | WO-01/36403 | 5/2001 |
| WO | WO-2004/080950 | 9/2004 |
| WO | WO-2004/082677 | 9/2004 |
| WO | WO-2007/002325 | 1/2007 |
| WO | WO-2007/124423 | 11/2007 |
| WO | WO-2010/036316 | 4/2010 |
| WO | WO-2011-084642 | 7/2011 |

OTHER PUBLICATIONS

Lamberto et al. Journal of Biological Chemistry,vol. 286, p. 32036-32044 (2011).*
Amer et al., "Inhibitors of α-synuclein oligomerization and toxicity: a future therapeutic strategy for Parkinson's disease and related disorders," Exp. Brain Res. (2006) 173:223-233.
Amijee et al., "Inhibitors of protein aggregation and toxicity," Biochem. Soc. Trans. (2009) 37(4):692-696.
Bagshawe, "Antibody-Directed Enzyme Prodrug Therapy: A Review," Drug Dev. Res. (1995) 34:220-230.
Begum et al., "Curcumin Structure-Function, Bioavailability, and Efficacy in Models of Neuroinflammation and Alzheimer's Disease," J. Pharmacol. Exp. Ther. (2008) 326(1):196-208.
Berge et al., "Pharmaceutical salts," J. Pharm. Sci. (1977) 66(1):1-19.
Bertolini et al., "A new rational hypothesis for the pharmacophore of the active metabolite of leflunomide, a potent immunosuppressive drug," J. Med. Chem. (1997) 40(13):2011-2016.
Bodor, "Novel Approaches to the Design of Safer Drugs: Soft Drugs and Site-Specific Chemical Delivery Systems," Adv. Drug Res. (1984) 13:255-331.
Brooks, "Positron Emission Tomography and Single-Photon Emission Computed Tomography in Central Nervous System Drug Development," NeuroRx (2005) 2:226-236.
Cole et al., "Neuroprotective Effects of Curcumin," Adv. Exp. Med. Biol. (2007) 595:197-212.
Fleming et al., "Early and Progressive Sensorimotor Anomalies in Mice Overexpressing Wild-Type Human α-Synuclein," J. Neurosci. (2004) 24(42):9434-9440.
Hamaguchi et al., "Phenolic Compounds Prevent Alzheimer's Pathology through Different Effects on the Amyloid-β Aggregation Pathway," Am. J. Pathol. (2009) 175(6):2557-2565.

(Continued)

Primary Examiner — Emily Bernhardt
(74) Attorney, Agent, or Firm — Morrison & Foerster LLP

(57) ABSTRACT

The present invention relates to certain phenyl-urea and phenyl-carbamate derivatives comprising a bicyclic heteroaryl group, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, and multiple system atrophy.

18 Claims, 3 Drawing Sheets

(56) References Cited

OTHER PUBLICATIONS

Hashimoto et al., "β-Synuclein Inhibits α-Synuclein Aggregation: A Possible Role as an Anti-Parkinsonian Factor," Neuron (2001) 32:213-223.

Katritzky et al., "A New Synthetic Method for the 2-Substitution of N-Unsubstituted Benzimidazoles: Formaldehyde as a Versatile Protecting Agent for Heterocyclic NH," J. Org. Chem. (1989) 54:2949-2952.

Marambaud et al., "Resveratrol Promotes Clearance of Alzheimer's Disease Amyloid-β Peptides," J. Biol. Chem. (2005) 280(45):37377-37382.

Masliah et al., "Dopaminergic loss and inclusion body formation in α-synuclein mice: implications for neurodegenerative disorders," Science (2000) 287(5456):1265-1269.

Ono et al., "Anti-amyloidogenic activity of tannic acid and its activity to destabilize Alzheimer's β-amyloid fibrils in vitro," Biochim. Biophys. Acta (2004) 1690:193-202.

Ono et al., "Curcumin Has Potent Anti-Amyloidogenic Effects for Alzheimer's β-Amyloid Fibrils In Vitro," J. Neurosci. Res. (2004) 75:742-750.

Ono et al., "Potent anti-amyloidogenic and fibril-destabilizing effects of polyphenols in vitro: implications for the prevention and therapeutics of Alzheimer's disease," J. Neurochem. (2003) 87:172-181.

Richard et al., "Neuroprotective properties of resveratrol and derivatives," Ann. N. Y. Acad. Sci. (2011) 1215:103-108.

Rockenstein et al., "Differential neuropathological alterations in transgenic mice expressing α-synuclein from the platelet-derived growth factor and Thy-1 promoters," J. Neurosci. Res. (2002) 68(5):568-578.

Shan et al., "Prodrug strategies based on intramolecular cyclization reactions," J. Pharm. Sci. (1997) 86(7):765-767.

Shimizu et al., "Modern Synthetic Methods for Fluorine-Substituted Target Molecules," Angew. Chem. Int. Ed. Eng. (2005) 44:214-231.

Supplementary European Search Report for EP 13768915.4, mailed Jul. 20, 2015, 12 pages.

* cited by examiner

PHENYL-UREA AND PHENYL-CARBAMATE DERIVATIVES AS INHIBITORS OF PROTEIN AGGREGATION

CROSS-REFERENCE TO RELATED APPLICATIONS

This application is a U.S. National Stage of International Application No. PCT/US2013/032552 filed on Mar. 15, 2013 which claims the benefit of U.S. Provisional Application 61/616,771 filed on Mar. 28, 2012. The contents of these applications are incorporated herein by reference in their entirety.

TECHNICAL FIELD

The present invention relates to certain phenyl-urea and phenyl-carbamate derivatives, pharmaceutical compositions containing them, and methods of using them, including methods for preventing, reversing, slowing, or inhibiting protein aggregation, and methods of treating diseases that are associated with protein aggregation, including neurodegenerative diseases such as Parkinson's disease, Alzheimer's disease, Lewy body disease, and multiple system atrophy.

BACKGROUND ART

Neurodegenerative disorders of the aging population such as Alzheimer's disease (AD), Parkinson's disease (PD), and fronto-temporal dementia (FTD), affect over 20 million people in the United States and European Union alone and rank among the top causes of death for the elderly. A common feature among these neurological disorders is the chronic accumulation of proteins into neurotoxic aggregates. Each disease is characterized by the specific neuronal populations that are affected, the particular protein aggregates that are involved, and the clinical features that result from the neuronal degeneration.

Studies suggest that the initial stages of protein aggregation involve mutation or post-translational modification (e.g., nitrosilation, oxidation) of the target protein, which then adopts an abnormal conformation that facilitates interactions with similarly misfolded proteins. The abnormal proteins then aggregate to form dimers, trimers, and higher-order multimers, also termed "soluble oligomers," which may disrupt synaptic function. Additionally, the aggregates may then anchor in the cell membrane and form globular oligomers (which in turn can form pores in the membrane) and/or protofibrils or fibrils. These larger, insoluble fibrils may function as reservoirs of the bioactive oligomers.

The particular proteins implicated in these neurodegenerative diseases vary in identity and source. For example, in AD, the neurotoxic aggregates are composed of the secreted protein amyloid-beta (A(β)). In idiopathic Parkinson's disease (IPD), dementia with Lewy bodies (LBD), PD dementia (PDD), and multiple system atrophy (MSA), the neurotoxic aggregates are composed of α-synuclein (SYN), which is a synaptic protein that is intracellular under normal conditions. In FTD and amyotrophic lateral sclerosis (ALS), neurotoxic aggregates originate from other intracellular proteins such as tau, TDP-43, or SOD1. For certain diseases, such as AD, SYN aggregates with the primary protein. Thus, compounds that interferer with SYN aggregation may impact neurodegenerative pathologies of various etiologies.

Two mechanisms are implicated in these neurodegenerative processes. In the first, the misfolded and/or aggregated proteins anchor to the various cell membrane structures. Binding of the misfolded or aggregated molecules to the plasma membrane or the membranes of organelles (e.g., mitochondria or lysosomes) may interfere with protein transcription, autophagy, mitochondrial function, and pore formation. By way of example, neurotoxic SYN aggregates and interacts with lipids in cell membranes, by a specific portion of the c-terminal region of the synuclein protein. Compounds that bind to this region can inhibit protein-protein or protein-lipid interactions and can therefore be used to block neurotoxic SYN oligomerization and membrane interaction. In the second process, aggregated protein is released from the anchored subunit and propagates to adjacent cells. This cell-to-cell propagation of toxic protein aggregates may then underlie the anatomic progression of neurodegeneration and worsening of symptoms. Small molecule drugs that interact with the target proteins may limit release and/or propagation, and therefore reduce the neurotoxic effects of aggregated proteins. Such compounds may therefore provide new therapies for AD, PD, LBD, MSA, and related neurodegenerative conditions.

There remains a need for inhibitors of protein aggregation with desirable pharmaceutical properties. Certain phenyl-urea and carbamate derivatives have been found in the context of this invention to have protein aggregation modulating activity.

SUMMARY OF THE INVENTION

In one aspect, the invention relates to a chemical entity of the following Formula (I):

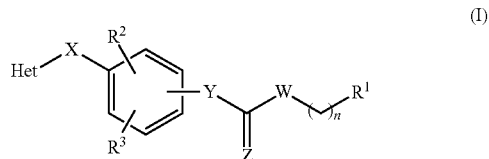

wherein
Het is a bicyclic heteroaryl in which at least one ring atom is a N, and said heteroaryl is unsubstituted or is substituted with one or more $R^a$ substituents;
  wherein each $R^a$ is independently hydroxyl, halo, amino, cyano, nitro, $C_{1-4}$alkyl, haloalkyl, $C_{1-4}$alkoxy, or halo-$C_{1-4}$alkoxy;
X is —$CH_2$—$R^z$—, wherein $R^z$ is absent, —$CH_2$—, —O—, —S—, or —NH—;
one of W and Y is NH and the other is O or NH;
Z is O or S;
$R^1$ is —$NR^bR^c$; guanidino; a monocyclic heteroaryl in which at least one ring atom is a N, and said heteroaryl is unsubstituted or is substituted with one or more $R^d$ substituents; or a monocyclic heterocycloalkyl, in which at least one ring atom is a N, and said heterocycloalkyl is unsubstituted or is substituted with one or more $R^e$ substituents;
  wherein $R^b$ and $R^c$ are each independently H or $C_{1-4}$alkyl;
  each $R^d$ is independently hydroxyl, halo, amino, cyano, nitro, $C_{1-4}$alkyl, haloalkyl, $C_{1-4}$alkoxy, or halo-$C_{1-4}$alkoxy; and
  each $R^e$ is independently hydroxyl, halo, amino, cyano, nitro, $C_{1-4}$alkyl, haloalkyl, $C_{1-4}$alkoxy, halo-$C_{1-4}$alkoxy, —C(O)$C_{1-4}$alkyl, or —$CO_2C_{1-4}$alkyl;
n is 0, 1, 2, 3, or 4;

$R^2$ is absent or is hydroxyl, methoxy, or trifluoromethoxy; and $R^3$ is $C_{1-6}$alkyl, $C_{1-6}$alkoxy or $C_{3-8}$cycloalkoxy, wherein said cycloalkoxy is unsubstituted or substituted with one or more substituents independently selected from the group consisting of hydroxyl, halo, amino, cyano, nitro, $C_{1-4}$alkyl, haloalkyl, $C_{1-4}$alkoxy, and halo-$C_{1-4}$alkyl;

or a pharmaceutically acceptable salt thereof.

In certain embodiments, the compound of Formula (I) is a compound selected from those species described or exemplified in the detailed description below.

In a further aspect, the invention relates to a pharmaceutical composition comprising at least one compound of Formula (I) or a pharmaceutically acceptable salt thereof. Pharmaceutical compositions according to the invention may further comprise a pharmaceutically acceptable excipient. The invention is also a compound of Formula I or a pharmaceutically acceptable salt thereof for use as a medicament.

In another aspect, the invention is directed to a method of treating a neurodegenerative disease or condition associated with protein aggregation comprising administering to a subject in need of such treatment an effective amount of at least one compound of Formula (I) or a pharmaceutically acceptable salt thereof.

In another aspect, the invention is directed to a method of treating a disease or medical condition associated with protein aggregation, comprising administering to a subject in need of such treatment an effective amount of at least one compound of Formula (I) or a pharmaceutically acceptable salt thereof. The invention is also directed at use of a compound of Formula I in the preparation of a medicament for the treatment of such diseases and medical conditions, and the use of such compounds and salts for treatment of such diseases and medical conditions.

In yet another aspect, the invention relates to a method of interfering with the accumulation of protein or peptide aggregation in a cell, or preventing, slowing, reversing, or inhibiting protein or peptide aggregation in a cell, comprising contacting the cell with an effective amount of at least one compound of Formula (I) or a salt thereof, and/or with at least one pharmaceutical composition of the invention, wherein the contacting is in vitro, ex vivo, or in vivo.

Additional embodiments, features, and advantages of the invention will be apparent from the following detailed description and through practice of the invention.

For the sake of brevity, the disclosures of the publications cited in this specification, including patents, are herein incorporated by reference.

DETAILED DESCRIPTION OF THE INVENTION

Figure 1:
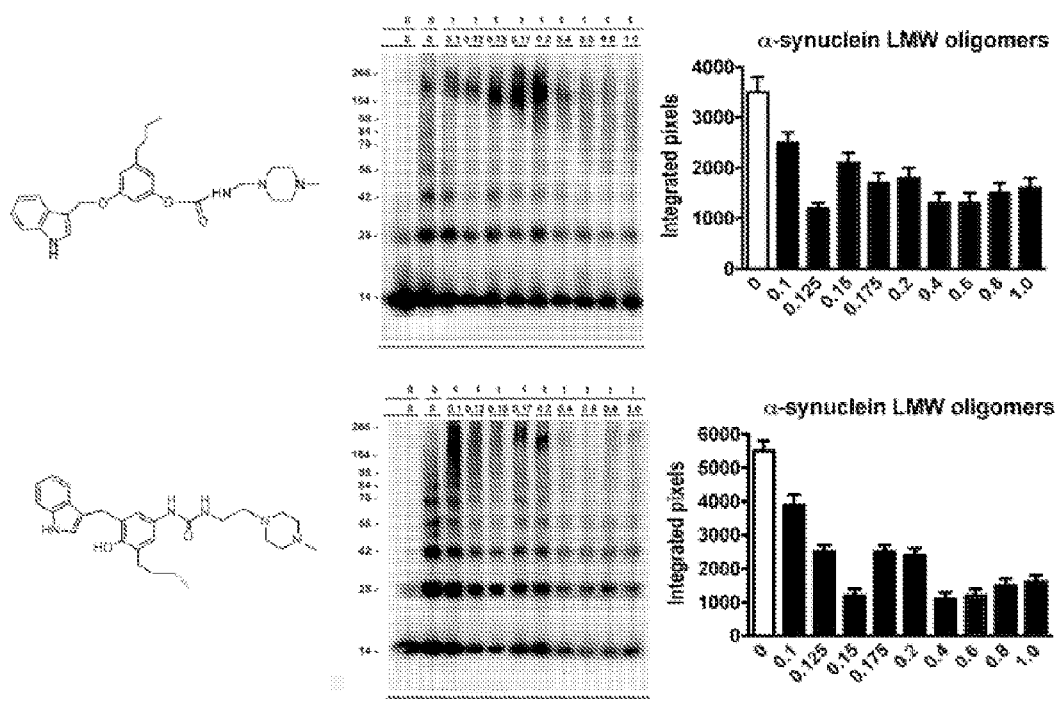
FIG. 1 depicts the effects of Example 2 on synuclein in a cell free in vitro system by immunoblot.

In some embodiments of Formula (I), Het is an 8-membered bicyclic heteroaryl with at least one nitrogen ring atom. In other embodiments, Het is 1H-indolyl, 1H-benzimidazolyl, 5H-pyrrolo[2,3-b]pyrazinyl, or 1H-imidazo[4,5-b]pyrazinyl.

In some embodiments, X is —$CH_2$—, —$CH_2CH_2$—, —$CH_2O$—, or —$CH_2NH$—. In other embodiments, X is —$CH_2$—, —$CH_2CH_2$—, or —$CH_2O$—.

In some embodiments, W is O and Y is NH. In other embodiments, W is NH and Y is O. In further embodiments, W and Y are both NH.

In some embodiments, Z is O.

In some embodiments, $R^1$ is amino, methylamino, dimethylamino, or guanidino, or is a pyrrolyl, imidazolyl, pyrazolyl, pyridinyl, pyrimidinyl, pyrazinyl, pyridazinyl, oxazolyl, thiazolyl, isoxazolyl, isothiazolyl, triazolyl, or tetrazolyl, each unsubstituted or substituted with one or two $R^d$ substituents; or a pyrrolidinyl, piperidinyl, piperazinyl, azepanyl, morpholinyl, thiomorpholinyl, oxo-thiomorpholinyl, or dioxo-thiomorpholinyl, each unsubstituted or substituted with one or two $R^e$ substituents. In other embodiments, $R^1$ is amino or guanidino; or a pyrrolyl, imidazolyl, piperidinyl, or piperazinyl, each unsubstituted or substituted with one or two $C_{1-4}$alkyl groups.

In some embodiments, n is 2.

In some embodiments, $R^2$ is absent or is OH.

In another embodiment, $R^3$ is methyl, ethyl, propyl, isopropyl, butyl, isobutyl, sec-butyl, tert-butyl, pentyl, methoxy, ethoxy, propoxy, isopropoxy, butoxy, cyclopropyloxy, cyclobutyloxy, cyclopentyloxy, or cyclohexyloxy. In other embodiments, $R^3$ is ethyl, propyl, isopropyl, butyl, propoxy, isopropoxy, cyclopropyloxy, cyclopentyloxy, or cyclohexyloxy. In still other embodiments, $R^3$ is ethyl or butyl.

In a further embodiment of the present invention, a compound of Formula II is provided:

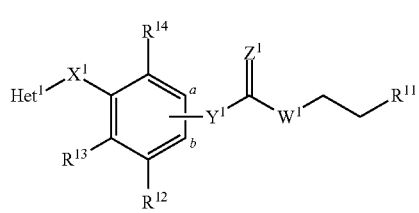

(II)

wherein $Het^1$ is a bicyclic heteroaryl in which at least one ring atom is a N;

$X^1$ is —$(CH_2)_{1-2}$— or —$CH_2O$—;

one of $W^1$ and $Y^1$ is NH and the other is O or NH;

$Y^1$ is attached to the phenyl at the "a" or "b" position;

$Z^1$ is O or S;

$R^{11}$ is amino; a monocyclic heteroaryl in which at least one ring atom is a N; or a monocyclic heterocycloalkyl in which at least one ring atom is a N, and said heterocycloalkyl is unsubstituted or is substituted with one or two $C_{1-4}$alkyl groups;

when $Y^1$ is attached at the "a" position of the phenyl ring,
$R^{12}$ is $C_{2-4}$alkyl, $C_{1-3}$alkoxy, or $C_{3-7}$cycloalkoxy;
$R^{13}$ is H or hydroxy; and
$R^{14}$ is H;

and when $Y^1$ is attached at the "b" position of the phenyl ring,
$R^{12}$ is H;
$R^{13}$ is $C_{2-4}$alkyl; and
$R^{14}$ is H or hydroxyl;

or a pharmaceutically acceptable salt thereof.

In a further embodiment, the invention relates to a chemical entity of the following Formula (I-A):

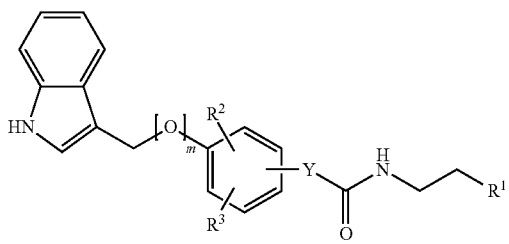

(I-A)

wherein

Y is O or NH;

R[1] is selected from the group consisting of amino, imidazolyl, and piperazin-1-yl substituted with one or two methyl groups;

R[2] is absent or is hydroxyl;

R[3] is $C_{1-6}$alkyl; and m is 0 or 1;

or a pharmaceutically acceptable salt thereof.

In a further embodiment, the invention relates to a compound of formula (I-A) in which at least one carbon is replaced with $^{11}C$, and/or at least one hydrogen is replaced with $^{18}F$. In other embodiments, one or two carbons are replaced with $^{11}C$. In other embodiments, one or two hydrogens are replaced with $^{18}F$.

In some embodiments, the $^{11}C$ is an indole or phenyl carbon. In other embodiments, $^{11}C$ is incorporated into the methylene group between the indole and phenyl rings or the ethylene group connected to R[1]. In other embodiments, the $^{11}C$ isotope is the carbonyl carbon. In still other embodiments, $^{11}C$ is incorporated into R[1] or R[3]. In still other embodiments, $^{11}C$ is a terminal methyl carbon (—$^{11}CH_3$).

In other embodiments, the $^{18}F$ is a substituent on the indole or phenyl group. In other embodiments, $^{18}F$ is incorporated into the methylene group between the indole and phenyl rings or the ethylene group connected to R[1]. In still other embodiments, $^{18}F$ is incorporated into R[1] or R[3]. In still other embodiments, $^{18}F$ is in a terminal methyl group (—$C(^{18}F)_x(H)_{3-x}$).

In other embodiments, the invention is directed to a compound selected from the group consisting of:

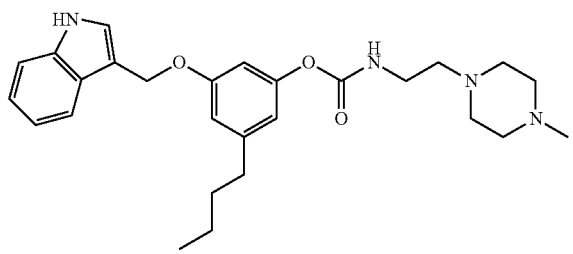

3-((1H-indol-3-yl)methoxy)-5-butylphenyl (2-(4-methylpiperazine-1-yl)ethyl)carbamate;

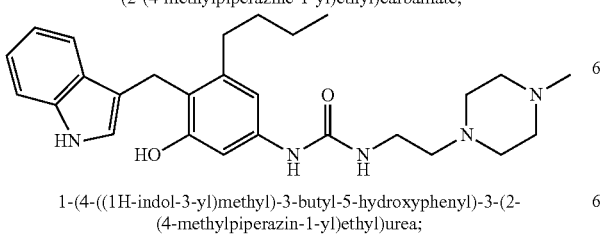

1-(4-((1H-indol-3-yl)methyl)-3-butyl-5-hydroxyphenyl)-3-(2-(4-methylpiperazin-1-yl)ethyl)urea;

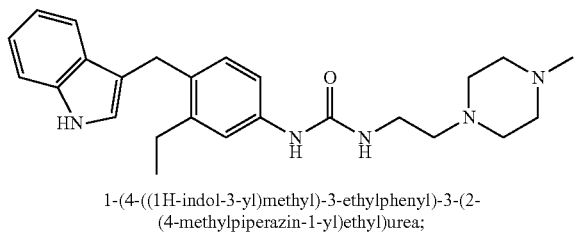

1-(4-((1H-indol-3-yl)methyl)-3-ethylphenyl)-3-(2-(4-methylpiperazin-1-yl)ethyl)urea;

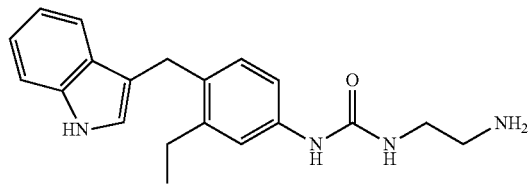

1-(4-((1H-indol-3-yl)methyl)-3-ethylphenyl)-3-(2-aminoethyl)urea;

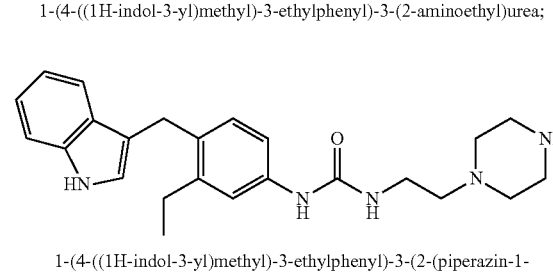

1-(4-((1H-indol-3-yl)methyl)-3-ethylphenyl)-3-(2-(piperazin-1-yl)ethyl)urea;

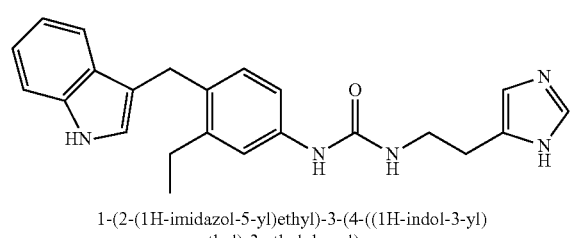

1-(2-(1H-imidazol-5-yl)ethyl)-3-(4-((1H-indol-3-yl)methyl)-3-ethylphenyl)urea;

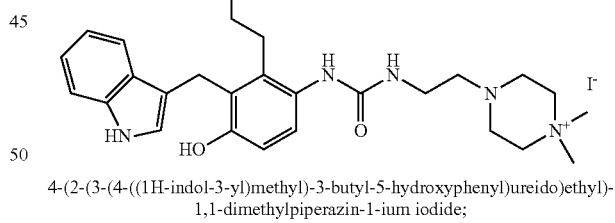

4-(2-(3-(4-((1H-indol-3-yl)methyl)-3-butyl-5-hydroxyphenyl)ureido)ethyl)-1,1-dimethylpiperazin-1-ium iodide;

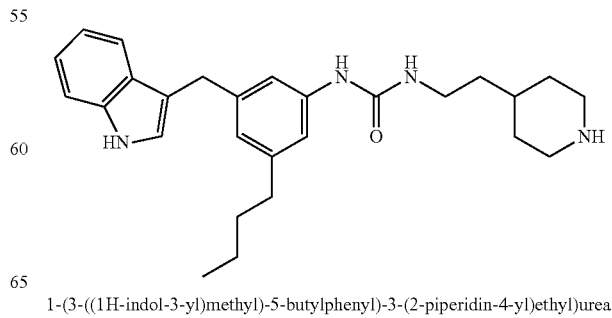

1-(3-((1H-indol-3-yl)methyl)-5-butylphenyl)-3-(2-piperidin-4-yl)ethyl)urea;

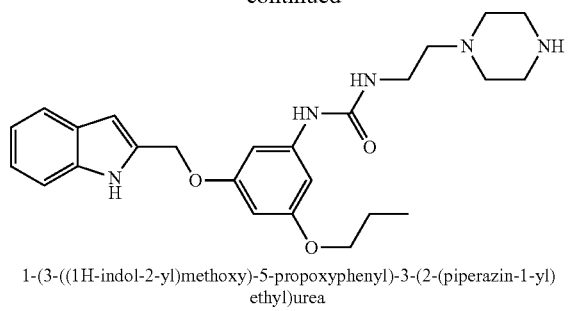

1-(3-((1H-indol-2-yl)methoxy)-5-propoxyphenyl)-3-(2-(piperazin-1-yl)ethyl)urea

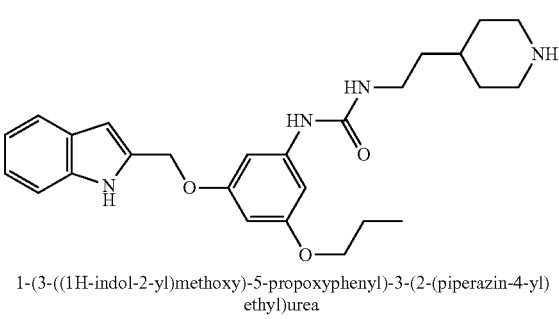

1-(3-((1H-indol-2-yl)methoxy)-5-propoxyphenyl)-3-(2-(piperazin-4-yl)ethyl)urea

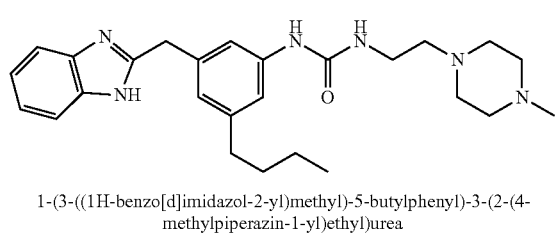

1-(3-((1H-benzo[d]imidazol-2-yl)methyl)-5-butylphenyl)-3-(2-(4-methylpiperazin-1-yl)ethyl)urea

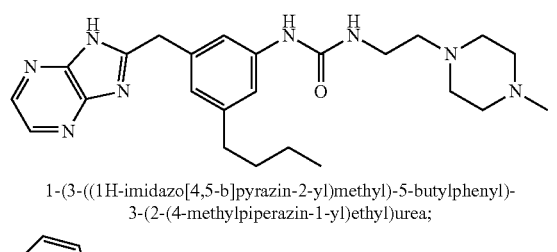

1-(3-((1H-imidazo[4,5-b]pyrazin-2-yl)methyl)-5-butylphenyl)-3-(2-(4-methylpiperazin-1-yl)ethyl)urea;

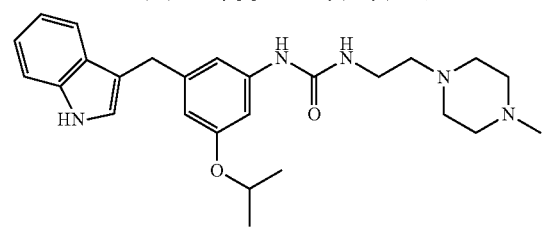

1-(3-((1H-indol-3-yl)methyl)-5-isopropoxyphenyl)-3-(2-(4-methylpiperazin-1-yl)ethyl)urea;

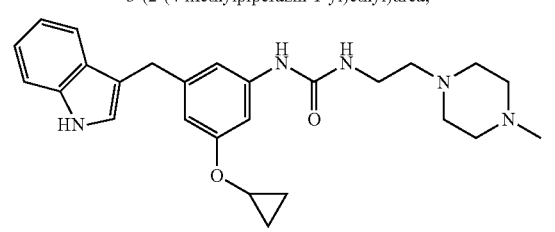

1-(3-((1H-indol-3-yl)methyl)-5-cyclopropoxyphenyl)-3-(2-(4-methylpiperazin-1-yl)ethyl)urea;

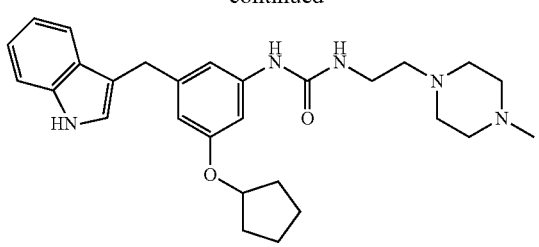

1-(3-((1H-indol-3-yl)methyl)-5-(cyclopentyloxy)phenyl)-3-(2-(4-methylpiperazin-1-yl)ethyl)urea;

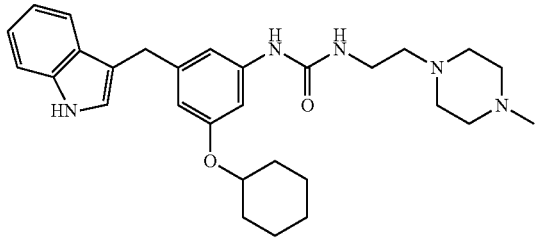

1-(3-((1H-indol-3-yl)methyl)-5-(cyclohexyloxy)phenyl)-3-(2-(4-methylpiperazin-1-yl)ethyl)urea;

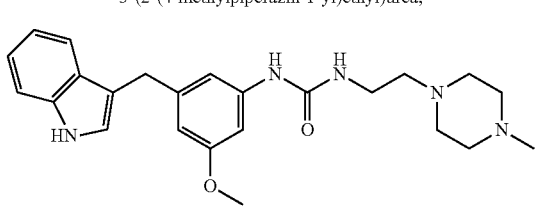

1-(3-((1H-indol-3-yl)methyl)-5-(methoxyphenyl)-3-(2-(4-methylpiperazin-1-yl)ethyl)urea;

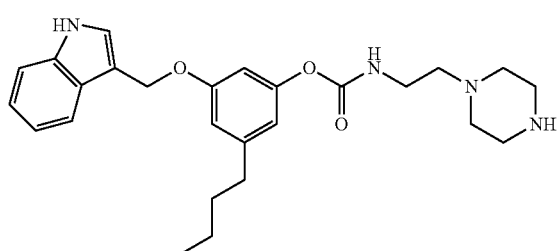

(3-((1H-indol-3-yl)methoxy)-5-butylphenyl (2-(piperazin-1-yl)ethyl)carbamate;

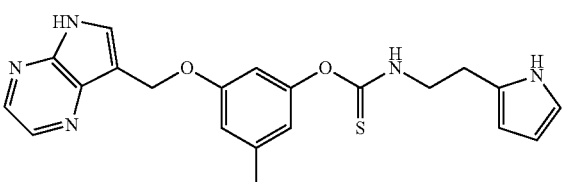

O-(3-((5H-pyrrolo[2,3-b]pyrazin-7-yl)methoxy)-5-propylphenyl) (2-(1H-pyrrol-2-yl)ethyl)carbamothioate;

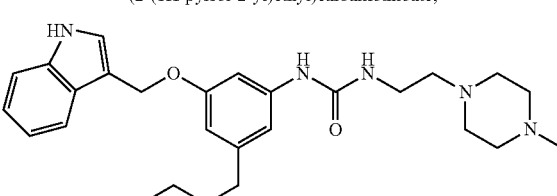

1-(3-((1H-indol-3-yl)methoxy)-5-butylphenyl)-3-(2-(4-methylpiperazin-1-yl)ethyl)urea;

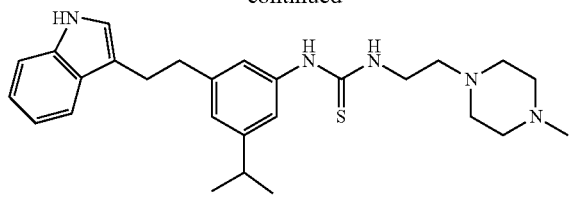

1-(3-(2-(1H-indol-3-yl)ethyl)-5-isopropylphenyl)-3-(2-(4-methylpiperazin-1-yl)ethyl)thiourea;

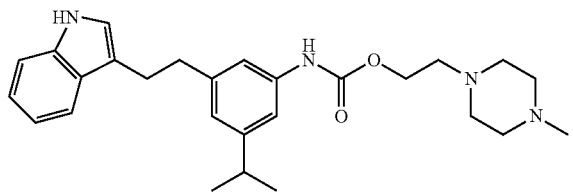

2-(4-methylpiperazin-1-yl)ethyl (3-(2-(1H-indol-3-yl)ethyl)-5-isopropylphenyl)carbamate;

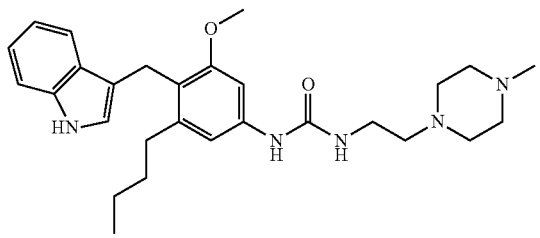

1-(4-((1H-indol-3-yl)methyl)-3-butyl-5-methoxyphenyl)-3-(2-(4-methylpiperazin-1-yl)ethyl)urea;

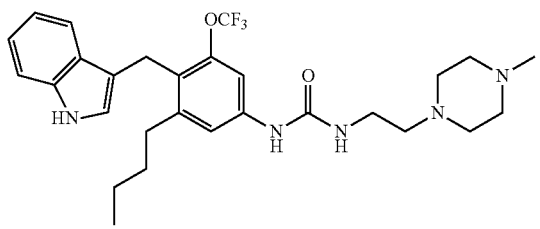

1-(4-((1H-indol-3-yl)methyl)-3-butyl-5-trifluoromethoxy)phenyl)-3-(2-(4-methylpiperazin-1-yl)ethyl)urea;

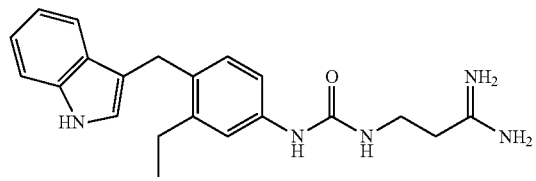

3-(3-(4-((1H-indol-3-yl)methyl)-3-ethylphenyl)ureido)propanimidamide;

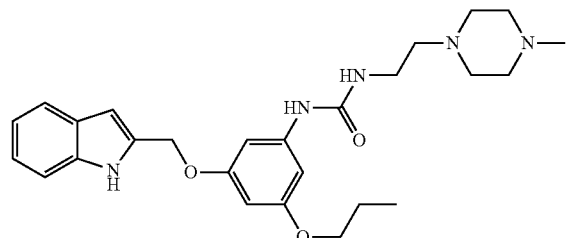

1-(3-((1H-indol-2-yl)methoxy)-5-propoxyphenyl)-3-(2-(4-methylpiperazin-1-yl)ethyl)urea;

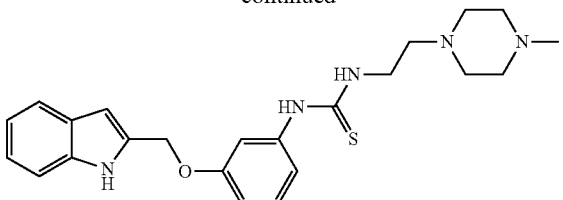

1-(3-((1H-indol-2-yl)methoxy)-5-propoxyphenyl)-3-(2-(4-methylpiperazin-1-yl)ethyl)thiourea; and

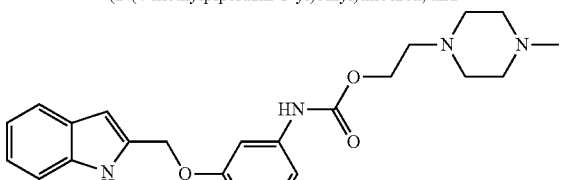

2-(4-methylpiperazin-1-yl)ethyl (3-((1H-indol-2-yl)methoxy)-5-propoxyphenyl)carbamate;

and pharmaceutically acceptable salts thereof.

In another aspect, the invention relates to a compound selected from the group consisting of:

3-((1H-Indol-3-yl)methoxy)-5-butylphenyl(2-(4-methylpiperazin-1-yl)ethyl)carbamate;
1-(4-((1H-Indol-3-yl)methyl)-3-butyl-5-hydroxyphenyl)-3-(2-(4-methylpiperazin-1-yl)ethyl)urea;
1-(4-((1H-indol-3-yl)methyl)-3-ethylphenyl)-3-(2-(4-methylpiperazin-1-yl)ethyl)urea;
1-(4-((1H-indol-3-yl)methyl)-3-ethylphenyl)-3-(2-aminoethyl)urea;
1-(4-((1H-indol-3-yl)methyl)-3-ethylphenyl)-3-(2-(4-methylpiperazin-1-yl)ethyl)urea;
1-(2-(1H-imidazol-5-yl)ethyl)-3-(4-((1H-indol-3-yl)methyl)-3-ethylphenyl)urea; and
4-(2-(3-(3-((1H-indol-3-yl)methyl)-5-butyl-4-hydroxyphenyl)ureido)ethyl)-1,1-dimethylpiperazin-1-ium iodide;
and pharmaceutically acceptable salts thereof.

General Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, the terms "including," "containing," and "comprising" are used in their open, non-limiting sense.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Chemical Definitions

The term "alkyl" refers to a straight- or branched-chain alkyl group having from 1 to 12 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" refers to an alkyl group as defined above, bonded to an oxygen atom. The alkoxy group is connected to the parent structure via the oxygen atom.

The term "amino" refers to an —NH$_2$ group.

The term "cycloalkyl" refers to a saturated or partially saturated, monocyclic, fused polycyclic, bridged polycyclic, or spiro polycyclic carbocycle having from 3 to 12 ring atoms per carbocycle. Illustrative examples of cycloalkyl groups include the following entities, in the form of properly bonded moieties:

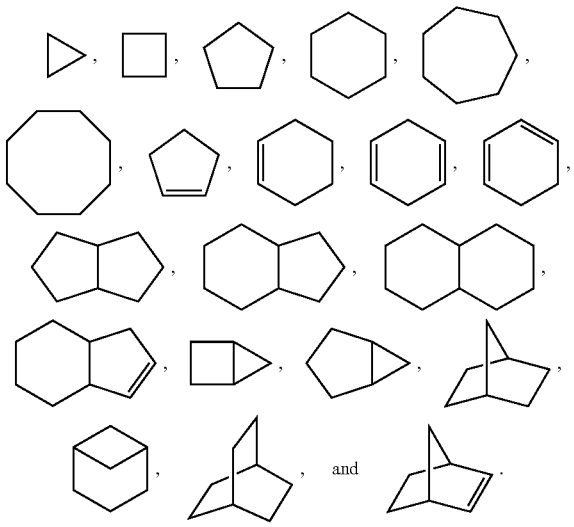

The term "cycloalkoxy" refers to a cycloalkyl as defined above, bound to an oxygen atom. The cycloalkoxy group is connected to the parent structure via the oxygen atom.

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

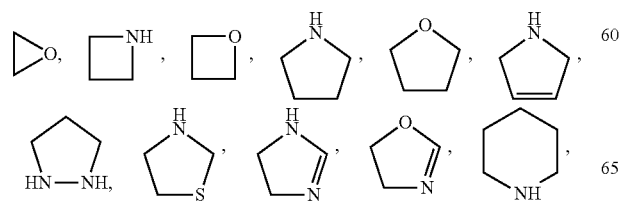

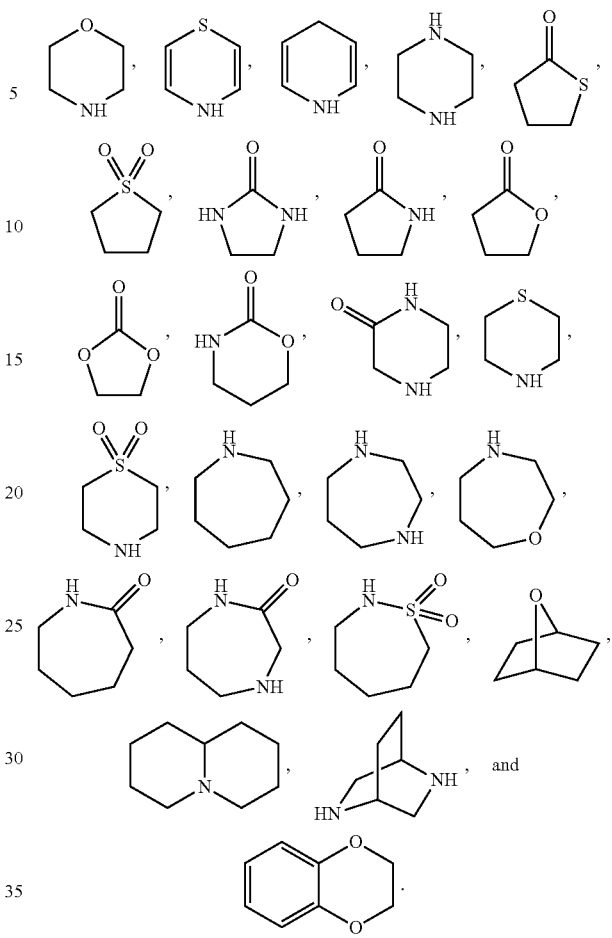

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

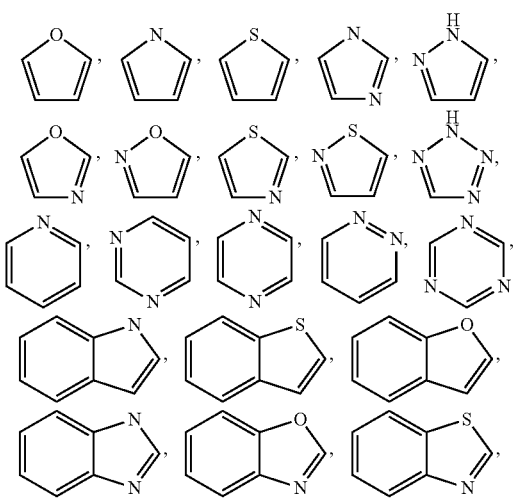

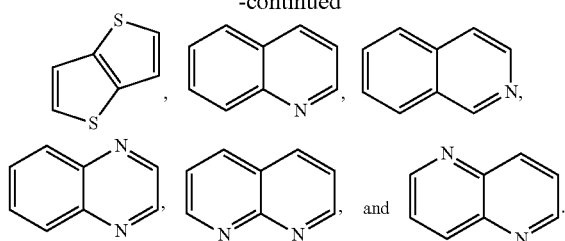

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine, or iodine. The term "halo" represents chloro, fluoro, bromo, or iodo. The term "haloalkyl" means an alkyl as defined above, substituted with one or more halogen atoms. The term "haloalkoxy" means an alkoxy as defined above, substituted with one or more halogen atoms.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. PET and SPECT studies may be performed as described, for example, by Brooks, D. J., "Positron Emission Tomography and Single-Photon Emission Computed Tomography in Central Nervous System Drug Development," *NeuroRx* 2005, 2(2), 226-236, and references cited therein. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention also includes pharmaceutically acceptable salts of the compounds represented by Formula (I), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," *J. Pharm. Sci.*, 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

For a compound of Formula (I) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

Exemplary neurodegenerative diseases that are characterized by protein aggregation include Alzheimer's Disease, Parkinson's Disease, fronto-temporal Dementia, Dementia with Lewy Bodies, PD Dementia, Multiple System Atrophy, and Amyotrophic Lateral Sclerosis.

In one aspect, the compounds and pharmaceutical compositions of the invention specifically target α-synuclein, β-amyloid, and/or tau protein aggregates. Thus, these compounds and pharmaceutical compositions can be used to prevent, reverse, slow, or inhibit aggregation of α-synuclein, β-amyloid, and/or tau proteins, and are used in methods of the invention to treat degenerative neurological diseases related to or caused by aggregation, e.g., such as aggregation of α-synuclein, β-amyloid, and/or tau proteins. Preferably, the methods of the invention target neurodegenerative diseases associated with aggregation of α-synuclein, β-amyloid, and/or tau protein. In preferred embodiments, methods of treatment target Parkinson's disease, Alzheimer's disease, Lewy body disease, or multiple system atrophy. The compounds, compositions, and method of the present invention are also used to mitigate deleterious effects that are secondary to protein aggregation, such as neuronal cell death.

In alternative aspects, the compounds, compositions, and methods of the invention are used to target synuclein aggregation. While the invention is not limited by any particular mechanism of action, synuclein aggregation is thought to be caused by a mis-alignment of the protein early in the disease process, which permits formation of protein multimers. As the number of monomer unites increases, the aggregated proteins can take on a pore-like shape, which can embed in the membrane of the neuron, disrupting ion flow and cell homeostasis.

In the inhibitory methods of the invention, an "effective amount" means an amount sufficient to reduce, slow the progression of, or reverse protein aggregation. Measuring the amount of aggregation may be performed by routine analytical methods such as those described below. Such modulation is useful in a variety of settings, including in vitro assays. In such methods, the cell is preferably a nerve cell.

In treatment methods according to the invention, an "effective amount" means an amount or dose sufficient to generally bring about the desired therapeutic benefit in subjects needing such treatment. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 ug to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Drug Combinations

The inventive compounds described herein may be used in pharmaceutical compositions or methods in combination with one or more additional active ingredients in the treatment of neurodegenerative disorders. For example, additional active ingredients are those that are known or discovered to be effective in treating neurodegenerative disorders, including those active against another target associated with the disease, such as but not limited to, a) compounds that address protein misfolding (such as drugs which reduce the production of these proteins, which increase their clearance or which alter their aggregation and/or propagation); b) compounds that treat symptoms of such disorders (e.g., dopamine replacement therapies); and c) drugs that act as neuroprotectants by complementary mechanisms (e.g., those targeting autophagy, those that are anti-oxidants, and those acting by other mechanisms such as adenosine A2A antagonists).

For example, additional active ingredients are those that are known or discovered to be effective in treating neurodegenerative disorders, including those active against another target associated with the disease, such as but not limited to, a) compounds that target different mechanisms of protein misfolding (such as aggregation and/or propagation); b) compounds that treat symptoms of such disorders (e.g., dopamine replacement therapies); and c) drugs that act as neuroprotectants by complementary mechanisms (e.g., those targeting autophagy, anti-oxidants, and adenosine A2A antagonists).

For example, compositions and formulations of the invention, as well as methods of treatment, can further comprise other drugs or pharmaceuticals, e.g., other active agents useful for treating or palliative for a degenerative neurological disease related to or caused by protein aggregation, e.g., synuclein, beta-amyloid and/or tau protein aggregation, e.g., Parkinson's disease, Alzheimer's Disease (AD), Lewy body disease (LBD) and multiple system atrophy (MSA), or related symptoms or conditions. For example, the pharmaceutical compositions of the invention may additional comprise one or more of such active agents, and methods of treatment may additionally comprise administering an effective amount of one or more of such active agents. In certain embodiments, additional active agents may be antibiotics (e.g., antibacterial or bacteriostatic peptides or proteins), e.g., those effective against gram positive or negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof. Additional active agents include those useful in such compositions and methods include dopamine therapy drugs, catechol-O-methyl transferase (COMT) inhibitors, monamine oxidase inhibitors, cognition enhancers (such as acetylcholinesterase inhibitors or memantine), adenosine 2A receptor antagonists, beta-secretase inhibitors, or gamma-secretase inhibitors. In particular embodiments, at least one compound of the present invention may be combined in a pharmaceutical composition or a method of treatment with one or more drugs selected from the group consisting of: tacrine (Cognex), donepezil (Aricept), rivastigmine (Exelon) galantamine (Reminyl), physostigmine, neostigmine, Icopezil (CP-118954, 5,7-dihydro-3-[2-[1-(phenylmethyl)-4-piperidinyl]ethyl]-6H-pyrrolo-[4,5-f-]-1,2-benzisoxazol-6-one maleate), ER-127528 (4-[(5,6-dimethoxy-2-fluoro-1-indanon)-2-yl]methyl-1-(3-fluorobenzyl)pipe-ridine hydrochloride), zanapezil (TAK-147; 3-[1-(phenylmethyl)piperidin-4-yl]-1-(2,3,4,5-tetrahydro-1H-1-benzazepin-8-yl)-1-propane fumarate), Metrifonate (T-588; (−)-R-.alpha.-[[2-(dimethylamino)ethoxy]methyl]benzo[b]thiophene-5-methanol hydrochloride), FK-960 (N-(4-acetyl-1-piperazinyl)-p-fluorobenzamide-hydrate), TCH-346 (N-methyl-N-2-pyropinyldibenz[b,f]oxepine-10-methan-amine), SDZ-220-581 ((S)-.alpha.-amino-5-(phosphonom-ethyl)-[1,1'-biphenyl]-3-propionic acid), memantine (Namenda/Exiba) and 1,3,3,5,5-pentamethylcyclohexan-1-amine (Neramexane), tarenflurbil (Flurizan), tramiprosate (Alzhemed), clioquinol, PBT-2 (an 8-hydroxyquinilone derivative), 1-(2-(2-Naphthyl)ethyl)-4-(3-trifluoromethyl-phenyl)-1,2,3,6-tetrahydropyr-idine, Huperzine A, posatire-lin, leuprolide or derivatives thereof, ispronicline, (3-amino-propyl)(n-butyl)phosphinic acid (SGS-742), N-methyl-5-(3-(5-isopropoxypyridinyl))-4-penten-2-amine (ispronicline), 1-decanaminium, N-(2-hydroxy-3-sulfopropyl)-N-methyl-N-octyl-, inner salt (zt-1), salicylates, aspirin, amoxiprin, benorilate, choline magnesium salicylate, diflunisal, faislamine, methyl salicylate, magnesium salicylate, salicyl salicylate, diclofenac, aceclofenac, acemetacin, bromfenac, etodolac, indometacin, nabumetone, sulindac, tolmetin, ibuprofen, carprofen, fenbufen, fenoprofen, flurbiprofen, ketoprofen, ketorolac, loxoprofen, naproxen, tiaprofenic acid, suprofen, mefenamic acid, meclofenamic acid, phenylbutazone, azapropazone, metamizole, oxyphenbutazone, sulfinprazone, piroxicam, lornoxicam, meloxicam, tenoxicam, celecoxib, etoricoxib, lumiracoxib, parecoxib, rofecoxib, valdecoxib, nimesulide, arylalkanoic acids, 2-arylpropionic acids (profens), N-arylanthranilic acids (fenamic acids), pyrazolidine derivatives, oxicams, COX-2 inhibitors, sulphonanilides, essential fatty acids, and Minozac (2-(4-(4-methyl-6-phenylpyridazin-3-yl)piperazin-1-yl)pyrimidine dihydrochloride hydrate), or a combination thereof. Such a combination may serve to increase efficacy, ameliorate other disease symptoms, decrease one or more side effects, or decrease the required dose of an inventive compound. The additional active ingredients may be administered in a separate pharmaceutical composition from a compound of the present invention or may be included with a compound of the present invention in a single pharmaceutical composition. The additional active ingredients may be administered simultaneously with, prior to, or after administration of a compound of the present invention.

Chemical Synthesis

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I). Isotopically labeled compounds as described herein are prepared according to the methods described below, using suitably labeled starting materials. Such materials are generally available from commercial suppliers of radiolabeled chemical reagents.

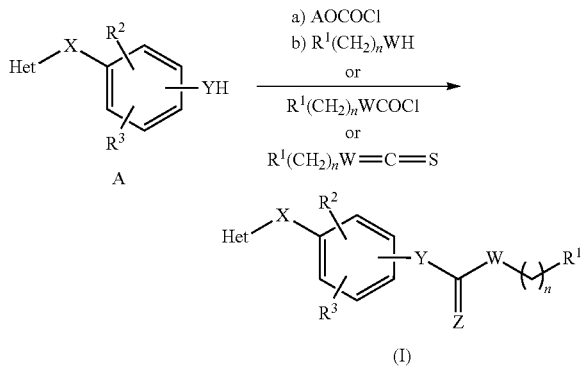

Scheme A

Compounds of Formula I may be prepared according to Scheme A, which demonstrates the introduction of the urea, carbamate, thiourea, or thiocarbamate arm of such compounds. Compounds A may be reacted with a suitable chloroformate reagent AOCOCl, followed by an R$^1$-containing alcohol or amine, to introduce a carbamate or urea. Alternatively, compounds A may be reacted with an integrated chloroformate reagent, $R^1(CH_2)_nWCOCl$, or a isocyanate reagent, $R^1(CH_2)_nW=C=S$. Typically, these coupling reactions are performed in the presence of a tertiary amine base, such as triethylamine or diisopropylethylamine, in a solvent such as dichloromethane.

Scheme B

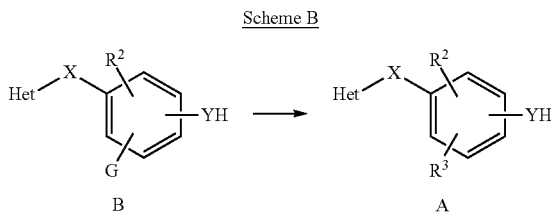

Compounds A may be prepared according to Scheme B, in which the $R^3$ substituent is introduced. Compounds B where G is OH are themselves compounds A. Such compounds may be alkylated with a suitable alkylating agent, such as an alkyl halide, or cycloalkyl halide, to form compounds in which $R_3$ is alkoxy or cycloalkoxy. Compounds B where G is —CHO or a derivative thereof, may be reacted with a suitable Wittig reagent, such as =PPh$_3^+$Br$^-$, to form compounds where G is an alkenyl group, which may then be reduced in the presence of hydrogen and a suitable catalyst to form compounds A in which $R_3$ is alkyl.

Scheme C

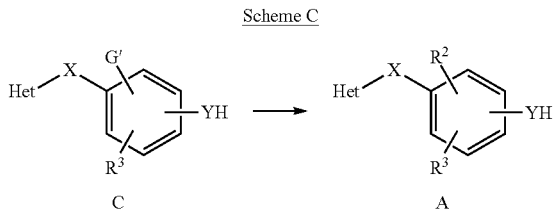

Compounds A may also be prepared according to Scheme C, in which the $R^2$ substituent is introduced. Compounds C in which G' is absent or is OH are themselves compounds A. Where G' is OH, such compounds C may be reacted with methyl iodide, under Mitsunobu conditions, to form a methoxy group $R^2$, or may be converted to a trifluoromethyl ether via the corresponding dithiocarbonate, for example, as described in Shimizu et al. *Angew. Chem. Int. Ed. Eng.* 2005, 44, 214-231.

Scheme D

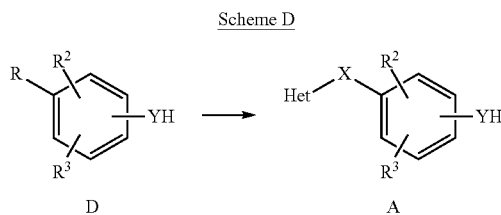

Compounds A (or analogs where $R_2$ and/or $R_3$ are G' and G, respectively), may be prepared as shown in Scheme D. Where R is OH, SH, or NH$_2$, such compounds may be alkylated with a suitable Het-containing reagent, such as Het-CH$_2$Br, Het-CH$_2$CH$_2$Br, or Het-CH$_2$CH$_2$Cl, and the like, to introduce the Het-X-subunit. Where the Het-X-group in compound A is linked to the phenyl ring via a carbon atom, the Het-X-group may be introduced using an aromatic substitution reaction on an appropriately substituted phenyl ring (see, for example, Example 2, below). In cases where Het is a benzimidazole ring, these compounds may be synthesized by preparing the 2-lithio benzimidazole and performing an alkylation reaction, for example, as described in Katritzky A. R.; Akutagawa K. *J. Org. Chem.* 1989, 54, 2949-2952. Alternatively, where R is —CH$_2$OH, a nucleophilic Het-group may be introduced via an alkylation reaction in the presence of a suitable acid such as trifluoroacetic acid (see, for example, Example 3, below).

EXAMPLES

The following examples are offered to illustrate but not to limit the invention.

Example 1

3-((1H-Indol-3-yl)methoxy)-5-butylphenyl(2-(4-methylpiperazin-1-yl)ethyl)carbamate

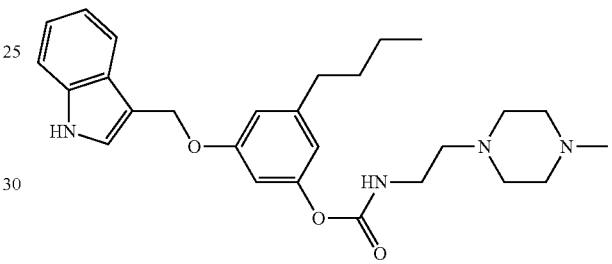

Step 1. To a solution of 1H-indole-3-carbaldehyde (29.2 g, 0.2 mol), 4-(dimethylamino)pyridine (1.28 g, 0.01 mol), and triethylamine (30.3 g, 0.3 mol) in dichloromethane (100 mL) was added dropwise di-tert-butyl dicarbonate (Boc$_2$O) (65.2 g, 0.2 mol) at 0° C. The mixture was stirred at room temperature overnight. Dichloromethane (100 mL) was added and the organic layer was washed with H$_2$O (3×50 mL) and brine (50 mL) and dried over anhydrous sodium sulfate. After filtration, the filtrate was concentrated to give tert-butyl 3-formyl-1H-indole-1-carboxylate (44 g, 90%). $^1$H NMR (400 MHz, CDCl$_3$) δ: 1.71 (s, 9H), 7.44-7.25 (m, 2H), 8.15 (d, 1H), 8.24 (s, 1H), 8.29 (d, 1H), 10.1 (s, 1H).

Step 2. To a solution of tert-butyl 3-formyl-1H-indole-1-carboxylate (44 g, 0.17 mol) in ethanol (50 mL) was added sodium borohydride (16.6 g, 0.45 mol) at 0° C. The mixture was stirred at room temperature for 3 hours. After filtration, the filtrate was evaporated to remove ethanol. The residue was partitioned between ethyl acetate (100 mL) and water (50 mL). The aqueous layer was extracted with ethyl acetate (2×50 mL). The combined organic layers were washed with brine (50 mL), dried over anhydrous sodium sulfate, and concentrated in vacuum to give tert-butyl 3-(hydroxymethyl)-1H-indole-1-carboxylate (40 g, 95%). $^1$H NMR (400 MHz, CDCl$_3$) δ: 1.59 (s, 9H), 4.77 (s, 2H), 7.19 (t, 1H), 7.25 (t, 1H), 7.51 (s, 1H), 7.57 (d, 1H), 8.06 (d, 1H).

Step 3. To a solution of triphenylphosphine (18.86 g, 72 mmol) in CCl$_4$ (150 mL), cooled to 0° C., Br$_2$ (3.34 mL, 66 mmol) was added slowly. The resulting orange-yellow suspension was stirred 20 min at 0° C. A solution of compound tert-butyl 3-(hydroxymethyl)-1H-indole-1-carboxylate (14.8 g, 60 mmol) in CCl$_4$ (50 mL) was added over 10 min. The resulting mixture was stirred at room temperature for 1 h. The solid was filtered off, and the filtrate was concentrated to give compound tert-butyl 3-(bromomethyl)-1H-indole-1-carboxylate (15.26 g, 82.3%). $^1$H NMR (400 MHz, CDCl$_3$) δ: 1.59 (s, 9H), 4.62 (s, 2H), 7.23 (t, 1H, J=0.8 Hz), 7.26-7.31 (m, 1H), 7.60-7.62 (m, 2H), 8.07 (d, 1H, J=7.6 Hz).

Step 4. A mixture of 1-methylpiperazine (9.0 g, 90 mmol), acetonitrile (60 mL), K$_2$CO$_3$ (60.0 g, 430.0 mmol), and 2-chloroacetonitrile (7.2 g, 95 mmol) was stirred at room temperature overnight. Ethyl acetate (100 mL) was added, and the suspension was filtered. The filtrate was concentrated in vacuo to give 2-(4-methylpiperazin-1-yl)acetonitrile as black oil (1.25 g, 99%), which was used directly in the subsequent step.

Step 5. To a stirred suspension of lithium aluminum hydride (3.3 g, 87 mmol) in dry THF (100 mL), cooled to 0° C., a solution of 2-(4-methylpiperazin-1-yl)acetonitrile (11.2 g, 80.4 mmol) in dry THF (300 mL) was slowly added. The mixture was stirred at room temperature for 1 h. The mixture was cooled in an ice bath, then H$_2$O (3.3 mL) and a 20% NaOH solution (3.3 mL) was added in sequence. After stirring for 20 min, the mixture was filtered and the solvent evaporated. The residue was dissolved in ethyl acetate and dried over anhydrous sodium sulfate. The solvent was evaporated to dryness to give 2-(4-methylpiperazin-1-yl) ethanamine (1.15 g, 99%) as an oil. $^1$H NMR (400 MHz, CDCl$_3$) δ: 2.21 (s, 3H), 2.20-2.60 (m, 10H), 2.71 (t, J=6.0 Hz, 2H).

Step 6. To a solution of n-C$_3$H$_7$PPh$_3$Br (13.2 g, 34.2 mmol) in dry THF (342 mL) was added n-BuLi (13.68 mL, 2.5 M) at 0° C. under nitrogen. The reaction mixture was stirred for 2 h at 0° C., then cooled to −78° C. and 3,5-dimethoxybenzaldehyde (5.7 g, 34.2 mmol) was added. The reaction mixture was allowed to heat at reflux overnight. The mixture was quenched with saturated aqueous NH$_4$Cl solution and extracted with ethyl acetate (2×500 mL). The organic layer was washed with water (500 mL), dried over anhydrous sodium sulfate, and concentrated. The residue was purified by column (eluting with 5:1 petroleum ether/ ethyl acetate) to give (E)-1-(but-1-en-1-yl)-3,5-dimethoxybenzene (5 g, 75.7%). $^1$H NMR (400 MHz, CDCl$_3$) δ: 1.12-1.05 (m, 3H), 2.40-2.20 (m, 2H), 3.80 (s, 6H), 5.69-5.63 (m, 1H), 6.37-6.27 (m, 2H), 6.45 (s, 1H), 6.52 (s, 1H).

Step 7. To a solution of (E)-1-(but-1-en-1-yl)-3,5-dimethoxybenzene (4.8 g, 25 mmol) in ethanol (50 mL) was added Pd/C (~10%). The reaction mixture was stirred for 3 h at 25° C. under hydrogen. After filtration through a pad of diatomaceous earth, the residue was concentrated to give 1-butyl-3,5-dimethoxybenzene (3.5 g, 72%). $^1$H NMR (400 MHz, CDCl$_3$) δ: 0.93 (t, 3H), 1.39-1.34 (m, 2H), 1.64-1.56 (m, 2H), 2.56 (t, 2H), 6.31 (s, 1H), 6.36 (s, 1H).

Step 8. To a solution of 1-butyl-3,5-dimethoxybenzene (7.5 g, 38.6 mmol) in dichloromethane (75 mL) was added drop-wise BBr$_3$ (24.2 g, 96.6 mol) at 0° C. The reaction mixture was stirred at room temperature overnight. The mixture was quenched with H$_2$O and neutralized with NaHCO$_3$. Dichloromethane (100 mL) was added and the organic layer was washed with water (2×50 mL), dried over anhydrous sodium sulfate, and concentrated. The residue was purified by column (eluting with 5:1 petroleum ether/ ethyl acetate) to give 5-butylbenzene-1,3-diol (5 g, 78%). $^1$H NMR (400 MHz, CDCl$_3$) δ: 0.91 (t, 3H), 1.33 (m, 2H), 1.57 (m, 2H), 2.49 (t, 2H), 4.64 (s, 2H), 6.17 (s, 1H), 6.24 (s, 2H).

Step 9. A solution of 5-butylbenzene-1,3-diol (640 mg, 3.8 mmol) and t-BuOK (851 mg, 7.6 mmol) in 10 mL of N,N-dimethylformamide was stirred for 30 min at room temperature. To this solution was added a solution of tert-butyl 3-(bromomethyl)-1H-indole-1-carboxylate (1.2 g, 3.8 mmol) in 10 mL of DMF. The reaction mixture was stirred for overnight and then diluted with 500 mL of dichloromethane. The reaction mixture was washed with brine (3×50 mL). The organic phase was concentrated to the crude product, which was purified by column (eluting with 1:1 petroleum ether/ethyl acetate) to give tert-butyl 3-((3-butyl-5-hydroxyphenoxy)methyl)-1H-indole-1-carboxylate (300 mg, 20%).

Step 10. To a solution of 4-nitrophenyl choroformate (500 mg, 2.5 mmol) and tert-butyl 3-((3-butyl-5-hydroxyphenoxy)methyl)-1H-indole-1-carboxylate (1 g, 2.5 mmol) in dichloromethane (20 mL) was added diisopropylethylamine (650 mg, 5 mmol). The solution was stirred for 30 min and then was treated with 2-(4-methylpiperazin-1-yl)ethanamine (1.4 g, 10 mmol) at room temperature. The reaction mixture was stirred at room temperature overnight and then was diluted with 100 mL of dichloromethane. The reaction mixture was washed with brine (3×50 mL). The organic phase was concentrated to the crude product, which was purified by preparative HPLC to afford tert-butyl 3-((3-butyl-5-(((2-(4-methylpiperazin-1-yl)ethyl)carbamoyl)oxy)phenoxy)methyl)-1H-indole-1-carboxylate (540 mg, 40%). $^1$H NMR (400 MHz, CDCl$_3$) δ: 0.837 (t, 3H), 1.27 (m, 2H), 1.48 (m, 2H), 1.59 (s, 9H), 2.49 (t, 2H), 2.74 (s, 3H), 3.16 (m, 2H), 3.52 (m, 10H), 5.08 (s, 2H), 6.17 (t, 1H), 6.50 (s, 1H), 6.58 (s, 1H), 6.64 (s, 1H), 7.19 (m, 1H), 7.27 (m, 1H), 7.56 (m, 2H), 8.07 (m, 1H).

Step 11. tert-Butyl 3-((3-butyl-5-(((2-(4-methylpiperazin-1-yl)ethyl)carbamoyl)oxy)phenoxy)methyl)-1H-indole-1-carboxylate (1.13 g, 2 mmol) in 5 M HCl-MeOH (20 mL) was stirred for 10 min at −78° C., and concentrated. The residue was purified by preparative HPLC to afford 3-((1H-indol-3-yl)methoxy)-5-butylphenyl(2-(4-methylpiperazin-1-yl)ethyl)carbamate (270 mg. $^1$H NMR (400 MHz, MeOD) δ: 0.92 (t, 3H), 1.34 (m, 2H), 1.56 (m, 2H), 2.50 (m, 4H), 2.66 (m, 7H), 3.01 (m, 4H), 3.31 (t, 2H), 3.96 (s, 2H), 6.40 (s, 1H), 6.55 (s, 1H), 6.79 (s, 1H), 6.97 (m, 2H), 7.28 (m, 1H), 7.67 (m, 1H).

Example 2

1-(4-((1H-Indol-3-yl)methyl)-3-butyl-5-hydroxyphenyl)-3-(2-(4-methylpiperazin-1-yl)ethyl)urea

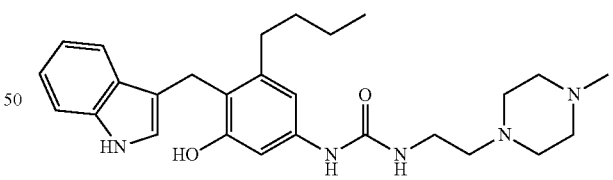

Step 1. n-BuLi (520 mL, 1.274 mol, 2.5 M solution in hexane) was added dropwise to 700 mL of dry methanol with vigorous stirring at −78° C. under N$_2$. The mixture was stirred for 30 min at room temperature after addition was complete. The solvent was removed under reduced pressure and the residue was dissolved in 1 L of hexamethylphosphoramide and cooled with an ice bath. 3,5-Dinitrobenzoic acid (100 g, 0.472 mol) was added to the stirring solution. The mixture was stirred for 5 h at room temperature and then stirred for 12 h at 80° C. The reaction mixture was cooled to room temperature and diluted with 2 L of H$_2$O, acidified with 600 mL of aqueous H$_2$SO$_4$ (6 M), and extracted with methyl tert-butyl ether (3 L). The organic phase was washed with brine, dried over Na$_2$SO$_4$, and concentrated to give 3-methoxy-5-nitrobenzoic acid (600 g, 81%, 8 batches). $^1$H NMR (400 MHz, DMSO) δ 3.91 (s, 3H), 7.78-7.79 (m, 1H), 7.90-7.91 (t, 1H), 8.17-8.18 (m, 1H).

Step 2. To a 3° C. solution of 3-methoxy-5-nitrobenzoic acid (80 g, 0.406 mol) in THF (700 mL) was added BH$_3$·THF (1 M in THF, 934 mL, 0.934 mmol). After stirring at 3° C. for 1 h, the mixture was warmed to room temperature and stirred for 12 h. The mixture was quenched by the addition of 112 mL of 1:1 acetic acid/H$_2$O. The solvents were removed and the residue was poured into 1.5 L of ice-cold saturated aqueous NaHCO$_3$ with vigorously stirring over 20 min. The solid was filtered and dried to afford (3-methoxy-5-nitrophenyl)methanol (310 g, 83%, 5 batches).

Step 3. To a solution of (3-methoxy-5-nitrophenyl)methanol (75 g, 0.41 mol) in CH$_2$Cl$_2$ (1.5 L) was added pyridinium dichromate (382 g, 1.02 mol) and silica gel (382 g) below 10° C. After stirring at room temperature for 3 h, TLC analysis showed the starting material was consumed completely (3:1 petroleum/ethyl acetate, R$_f$ 0.6). The mixture was purified by flash column chromatography using CH$_2$Cl$_2$ to afford 3-methoxy-5-nitrobenzaldehyde as a yellow solid (170 g, 76%, 3 batches).

Step 4. n-BuLi (148 mL, 0.37 mol, 2.5 M solution in hexane) was added dropwise, over 30 minutes, to a suspension of propyl triphenylphosphine bromide (42 g, 0.37 mol) in THF (500 mL) at ice bath temperature. A solution of 3-methoxy-5-nitrobenzaldehyde (67 g, 0.37 mol) in THF (300 mL) was added dropwise to the stirring solution. The mixture was stirred for 12 h. The mixture was poured into ice-water and extracted with ethyl acetate (1 L). The organic phase was washed with brine, dried over anhydrous Na$_2$SO$_4$, and the residue was subjected to flash column chromatography using petroleum ether/ethyl acetate (50:1) as eluent to afford (E)-1-(but-1-en-1-yl)-3-methoxy-5-nitrobenzene (103 g, 53%, 3 batches) as brown oil.

Step 5. To a solution of (E)-1-(but-1-en-1-yl)-3-methoxy-5-nitrobenzene (50 g, 0.282 mol) in methanol (1 L) was added Pd(OH)$_2$ (20 g) under Argon atmosphere. The mixture was stirred for 12 h under 50 psi of H$_2$ atmosphere at 45° C. After filtration, the solvent was removed under reduced pressure to afford 3-butyl-5-methoxyaniline (74 g, 73%, 2 batches).

Step 6. To a solution of 3-butyl-5-methoxyaniline (35 g, 196 mmol) in dichloromethane (500 mL) was added dropwise BBr$_3$ (121 g, 489 mmol) at -78° C. under N$_2$. The reaction mixture was stirred at room temperature for 6 h. The mixture was quenched with H$_2$O and neutralized with NaHCO$_3$. Dichloromethane (500 mL) was added and the organic layer was washed with brine (500 mL×3), dried over anhydrous Na$_2$SO$_4$, and concentrated. The residue was purified by flash column chromatography (eluting with 5:1 petroleum ether/ethyl acetate) to give 3-amino-5-butylphenol (40 g, 62%) as a brown solid.

Step 7. A solution of 1,1'-(azodicarbonyl)dipiperidine (9.2 g, 36.4 mmol) in THF was added dropwise over 1 h to a solution of 3-amino-5-butylphenol (5 g, 30.3 mmol), (1H-indol-3-yl)-methanol (5.3 g, 36.4 mmol) and PPh$_3$ (9.5 g, 36.4 mmol) in THF (80 mL) at ice bath temperature. The mixture was concentrated and purified by preparative HPLC to afford 2-((1H-indol-3-yl)methyl)-5-amino-3-butylphenol (10.5 g, crude, 8 batches).

Step 8. To a solution of 2-((1H-indol-3-yl)methyl)-5-amino-3-butylphenol (2 g, 6.8 mmol) and diisopropylethylamine (0.9 g, 6.8 mmol) in 40 mL of THF, was added 4-nitrophenyl chloroformate (1.4 g, 6.8 mmol). The solution was stirred for 30 min and then 2-(4-methylpiperazin-1-yl)ethanamine (1.9 g, 13.6 mmol) was added at room temperature. The reaction mixture was stirred at room temperature for 2 h. After the reaction mixture was concentrated, the residue was purified by preparative HPLC to afford 1-(4-((1H-indol-3-yl)methyl)-3-butyl-5-hydroxyphenyl)-3-(2-(4-methylpiperazin-1-yl)ethyl)urea (3.4 g, 36%, 3 batches) as a white solid. $^1$H NMR (400 MHz, DMSO) δ: 0.75-0.79 (t, 3H), 1.21 (m, 2H), 1.23 (m, 2H), 2.20 (m, 3H), 2.34-2.43 (m, 10H), 2.47-2.50 (m, 2H), 3.15-3.16 (d, J=6.0 Hz, 2H), 3.86 (s, 2H), 5.95 (s, 1H), 6.54-6.55 (d, J=2.0 Hz, 1H), 6.66 (d, J=2.0 Hz, 1H), 6.90 (s, 1H), 6.95 (d, J=2.0 Hz, 1H), 7.00 (s, 1H), 7.26 (d, J=8.4 Hz, 1H), 7.55 (d, J=7.6 Hz, 1H), 8.38 (s, 1H), 9.10 (s, 1H), 10.60 (d, J=1.6 Hz, 1H).

Example 3

1-(4-((1H-indol-3-yl)methyl)-3-ethylphenyl)-3-(2-(4-methylpiperazin-1-yl)ethyl)urea

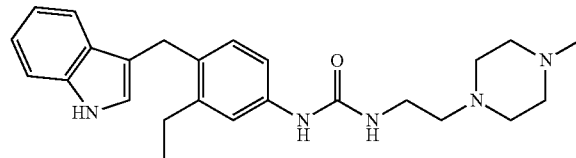

Step 1. To a solution 2-bromo-4-nitrobenzoic acid (100.0 g, 0.4 mol) and 1,8-diazabicyclo[5.4.0]undec-7-ene (80 g, 0.6 mmol) in acetonitrile (500 mL) was added MeI (120 g, 0.8 mol) dropwise at 0° C. The resulting mixture was stirred at 25° C. for 12 h. The mixture was concentrated and diluted with 300 mL CH$_2$Cl$_2$, washed with 2 N HCl (3×100 mL), 2 N NaOH (2×100 mL), and brine, dried over anhydrous Na$_2$SO$_4$, and concentrated to give methyl 2-bromo-nitrobenzoate (104 g, 100%) as a white solid. $^1$H NMR (400 MHz, CDCl$_3$) δ: 4.01 (s, 3H), 7.93-7.95 (d, J=8.8 Hz, 1H), 8.22-8.24 (m, 1H), 8.53-8.54 (m, 1H).

Step 2. A mixture of methyl 2-bromo-nitrobenzoate (22.0 g, 84.6 mmol), vinylboronic anhydride pyridine complex (20.2 g, 84.1 mmol), Pd(PPh$_3$)$_4$ (4.9 g, 4.33 mmol), and K$_2$CO$_3$ (46.5 g, 336.8 mmol) in toluene/ethanol (1:1, 820 mL) was stirred at 90° C. under N$_2$ for 2 h. The reaction mixture was concentrated and the residue was partitioned between ethyl acetate and water. The organic layer was dried over anhydrous Na$_2$SO$_4$ and concentrated, and the residue was purified by column chromatography (10:1 petroleum ether/ethyl acetate) to give ethyl 4-nitro-2-vinylbenzoate (14 g, 76.6%) as a yellow solid. $^1$H NMR (400 MHz, CDCl$_3$) δ: 1.32-1.36 (m, 3H), 4.31-4.36 (m, 2H), 2.62 (s, 3H), 5.41-5.44 (d, 1H), 5.71-5.75 (d, 1H), 7.33-7.37 (m, 1H), 7.88-7.90 (d, J=8 Hz, 1H), 7.98-8.01 (m, 1H), 8.27 (s, 1H).

Step 3. A mixture of ethyl 4-nitro-2-vinylbenzoate (15.8 g, 71.5 mmol) and Pd(OH)$_2$ (8.0 g) in MeOH (300 mL) was stirred at 25° C. for 4 h under H$_2$. The reaction mixture was filtered through a pad of diatomaceous earth and the filtrate was concentrated to give ethyl-4-amino-2-ethylbenzoate (13.1 g, 95%) as a yellow solid. $^1$H NMR (400 MHz, CDCl$_3$) δ: 1.19-1.22 (t, 3H), 1.33-1.34 (m, 3H), 2.91-2.97 (q, 2H), 4.26-4.31 (q, 2H), 6.46-6.50 (m, 2H), 7.91-7.81 (d, J=8 Hz, 1H).

Step 4. To a solution of LiAlH$_4$ (7.8 g, 203.7 mmol) in THF (100 mL) was added ethyl-4-amino-2-ethylbenzoate (13.1 g, 67.8 mmol) in THF (100 mL) dropwise at 0° C.

under N₂. After the addition was complete, the reaction mixture was stirred at rt for 12 h. The reaction mixture was cooled and quenched with H₂O (7 mL), 15% NaOH (7.8 mL) and H₂O (24 mL). Then the solution was filtered and concentrated to give (4-amino-2-ethylphenyl)methanol (8.3 g, 81%) as a yellow solid. ¹H NMR (400 MHz, CDCl₃) δ: 1.19-1.30 (t, 3H), 2.64-2.72 (m, 2H), 4.61 (s, 2H), 7.52-7.54 (dd, J=2.4, 8 Hz, 1H), 7.12-7.14 (d, J=2.4 Hz, 1H), 7.12-7.14 (d, J=8 Hz, 1H).

Step 5. To a solution of (4-amino-2-ethylphenyl)methanol (8.37 g, 55.43 mmol) and 1H-indole (12.97 g, 110.86 mmol) in dichloroethane (200 mL) was added trifluoroacetic acid (1.4 mL). After addition, the reaction mixture was stirred at 50° C. for 12 h. The reaction mixture was washed with saturation NaHCO₃ and extracted with ethyl acetate. The organic layer was washed with brine, dried with anhydrous Na₂SO₄, and concentrated. The residue was purified by column chromatography (5:1 petroleum ether/ethyl acetate) to give 4-((1H-indol-3-yl)methyl)-3-ethylaniline (5.2 g, 37%) as a yellow solid. ¹H NMR (400 MHz, CDCl₃) δ: 1.08-1.11 (t, 3H), 2.51-2.56 (q, 2H), 3.93 (s, 2H), 6.39-6.42 (dd, J=2.4 Hz, J=8 Hz, 1H), 6.52 (d, J=2.4 Hz, 1H), 6.62-6.63 (m, 1H), 6.89-6.91 (d, J=8 Hz, 1H), 7.00-7.04 (m, 1H), 7.09-7.29 (m, 1H), 7.482-7.483 (m, 1H), 7.501-7.503 (d, J=2.4 Hz, 1H).

Step 6. To a solution of 4-((1H-indol-3-yl)methyl)-3-ethylaniline (0.8 g, 3.2 mmol) and 4-nitrophenyl carbonochloridate (0.64 g, 3.2 mmol) in THF was added diisopropylethylamine (0.4 g, 3.2 mmol) (16 mL) at 20° C. and the resulting solution was stirred for 30 min. Then 2-(4-methylpiperazin-1-yl)ethanamine (0.9 g, 6.4 mmol) was added to the solution. After the addition was complete, the mixture was stirred at 20° C. for 12 h. The mixture was concentrated and purified by preparative HPLC to give 1-(4-((1H-indol-3-yl)methyl)-3-ethylphenyl)-3-(2-(4-methylpiperazin-1-yl)ethyl)urea (0.33 g, 26%) as a yellow solid. ¹H NMR (400 MHz, MeOD) δ: 1.13-1.17 (t, 3H), 2.25 (s, 3H), 2.48-2.71 (m, 10H), 3.29-3.32 (m, 2H), 4.01 (s, 2H), 6.73 (s, 1H), 6.92-6.96 (m, 1H), 7.02-7.08 (m, 3H), 7.18 (s, 1H), 7.29-7.31 (d, J=8.0 Hz, 1H), 7.39-7.41 (d, J=7.6 Hz, 1H); MS (M+1⁺): 220.3.

Example 4

1-(4-((1H-indol-3-yl)methyl)-3-ethylphenyl)-3-(2-aminoethyl)urea

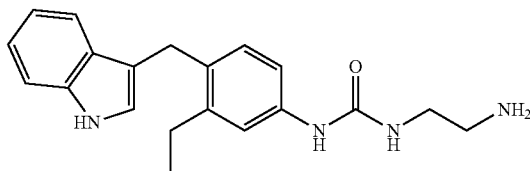 [SMILES: CCc1cc(NC(=O)NCCN)ccc1Cc1c[nH]c2ccccc12]

Step 1. To a solution of 4-((1H-indol-3-yl)methyl)-3-ethylaniline (0.8 g, 3.2 mmol) and 4-nitrophenyl carbonochloridate (0.64 g, 3.2 mmol) in THF was added diisopropylethylamine (0.4 g, 16 mL, 3.2 mmol) at 20° C. and the resulting solution was stirred for 30 min. To this solution was added tert-butyl(2-aminoethyl)carbamate (1.0 g, 6.4 mmol). After the addition, the mixture was stirred at 20° C. for 12 h. The mixture was concentrated and purified by preparative HPLC to give tert-butyl(2-(3-(4-((1H-indol-3-yl)methyl)-3-ethylphenyl)ureido)ethyl)carbamate (0.90 g, 64%) as a brown solid. ¹H NMR (400 MHz, CDCl₃) δ 1.17-1.20 (t, 3H), 1.42 (s, 9H), 2.64-2.69 (q, 2H), 3.33-3.25 (m, 2H), 3.36-3.35 (m, 2H), 4.05 (s, 2H), 5.00 (s, 1H), 5.22 (s, 1H), 6.42 (s, 1H), 6.70 (s, 1H), 6.99-7.00 (m, 1H), 7.02-7.12 (m, 2H), 7.35-7.37 (d, J=8.0 Hz, 1H), 7.53-7.56 (d, J=8.0 Hz, 1H), 7.96 (s, 1H).

Step 2. To a solution of tert-butyl(2-(3-(4-((1H-indol-3-yl)methyl)-3-ethylphenyl)ureido)ethyl)carbamate (0.8 g, 1.8 mmol) was added trifluoroacetic acid (9 mL) in CH₂Cl₂ (104 mL) at 0° C. slowly. After the addition was complete, the mixture was stirred at 10° C. for 12 h. The mixture was concentrated and purified by preparative HPLC to give 1-(4-((1H-indol-3-yl)methyl)-3-ethylphenyl)-3-(2-aminoethyl)urea (0.10 g, 16%) as a yellow solid. ¹H NMR (400 MHz, MeOD) δ: 1.14-1.17 (t, 3H), 2.63-2.69 (q, 2H), 2.75-2.78 (t, 2H), 3.25-3.28 (t, 2H), 4.02 (s, 2H), 6.73 (s, 1H), 6.92-6.96 (m, 1H), 7.04-7.08 (m, 3H), 7.19 (s, 1H), 7.29-7.31 (d, J=8.0 Hz, 1H), 7.40-7.42 (d, J=8.0 Hz, 1H). MS(M+1⁺): 337.1.

Example 5

1-(4-((1H-Indol-3-yl)methyl)-3-ethylphenyl)-3-(2-(piperazin-1-yl)ethyl)urea

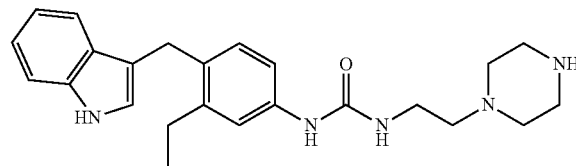 [SMILES: CCc1cc(NC(=O)NCCN2CCNCC2)ccc1Cc1c[nH]c2ccccc12]

Step 1. To a solution of 4-((1H-indol-3-yl)methyl)-3-ethylaniline (0.8 g, 3.2 mmol) and 4-nitrophenyl carbonochloridate (0.64 g, 3.2 mmol) in THF was added diisopropylethylamine (0.4 g, 16 mL, 3.2 mmol) at 25° C. and the resulting solution was stirred for 30 min. Then tert-butyl 4-(2-aminoethyl)piperazine-1-carboxylate (1.5 g, 6.4 mmol) was added to the above solution. The resulting mixture was stirred at 25° C. for 12 h. The mixture was concentrated and purified by preparative HPLC to give tert-butyl 4-(2-(3-(4-((1H-indol-3-yl)methyl)-3-ethylphenyl)ureido)ethyl)piperazine-1-carboxylate (1.3 g, 80%) as a white solid. ¹H NMR (400 MHz, CDCl₃) δ: 1.16-1.18 (t, 3H), 1.46 (s, 9H), 2.36-2.38 (m, 4H), 2.49-2.52 (t, 2H), 2.64-2.69 (q, 2H), 3.31-3.37 (m, 6H), 4.06 (s, 2H), 5.36 (s, 1H), 6.66 (s, 1H), 7.01-7.08 (m, 1H), 7.12-7.35 (m, 3H), 7.35-7.37 (d, J=8.0 Hz, 1H), 7.54-7.56 (d, J=8.0 Hz, 1H), 8.11 (s, 1H).

Step 2. To a solution of tert-butyl 4-(2-(3-(4-((1H-indol-3-yl)methyl)-3-ethylphenyl)ureido)ethyl)piperazine-1-carboxylate (0.8 g, 1.6 mmol) was added trifluoroacetic acid (8 mL) in CH₂Cl₂ (90 mL) at 0° C. slowly. After the addition was complete, the mixture was stirred at 10° C. for 12 h. The mixture was concentrated and purified by preparative HPLC to give 1-(4-((1H-indol-3-yl)methyl)-3-ethylphenyl)-3-(2-(4-methylpiperazin-1-yl)ethyl)urea (0.15 g, 23%) as a yellow solid. ¹H NMR (400 MHz, MeOD) δ 1.14-1.18 (t, 3H), 2.54-2.57 (t, 2H), 2.66-2.67 (m, 6H), 3.11-3.09 (m, 4H), 3.34-3.23 (m, 2H), 4.03 (s, 2H), 6.75 (s, 1H), 6.92-6.94 (m, 1H), 7.04-7.08 (m, 3H), 7.12 (s, 1H), 7.30-7.32 (d, J=8.0 Hz, 1H), 7.39-7.41 (d, J=8.0 Hz, 1H). MS (M+1⁺): 406.2.

Example 6

1-(2-(1H-imidazol-5-yl)ethyl)-3-(4-((1H-indol-3-yl)methyl)-3-ethylphenyl)urea

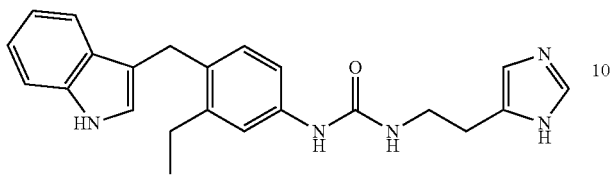

To a solution of 4-((1H-indol-3-yl)methyl)-3-ethylaniline (1.0 g, 4 mmol) and 4-nitrophenyl carbonochloridate (0.8 g, 4.0 mmol) in THF (20 mL) was added diisopropylethylamine (2.6 g, 20 mmol) at 25° C. and the resulting solution was stirred for 30 min. To the above solution was added 2-(1H-imidazol-5-yl)ethanamine dihydrochloride (0.9 g, 8.0 mmol) and the mixture was stirred at 25° C. for 12 h. The mixture was concentrated and purified by preparative HPLC to give 1-(2-(1H-imidazol-5-yl)ethyl)-3-(4-((1H-indol-3-yl)methyl)-3-ethylphenyl)urea (0.23 g, 15%) as a yellow solid. $^1$H NMR (400 MHz, MeOD) δ: 1.13-1.17 (t, 3H), 2.63-2.68 (q, 2H), 2.91-2.95 (t, 2H), 3.48-3.51 (t, 3H), 4.02 (s, 2H), 6.74 (s, 1H), 6.92-6.93 (m, 1H), 7.04-7.08 (m, 3H), 7.16 (s, 1H), 7.30-7.32 (d, J=8.0 Hz, 1H), 7.36-7.40 (m, 2H); MS (M+1$^+$): 388.2.

Example 7

4-(2-(3-(4-((1H-Indol-3-yl)methyl)-3-butyl-5-hydroxyphenyl)ureido)ethyl)-1,1-dimethylpiperazin-1-ium iodide

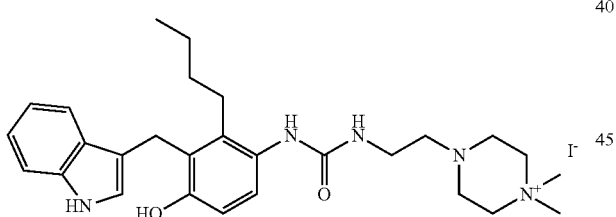

To a mixture of 1-(4-((1H-indol-3-yl)methyl)-3-butyl-5-hydroxyphenyl)-3-(2-(4-methylpiperazin-1-yl)ethyl)urea (250 mg, 0.54 mmol) and K$_2$CO$_3$ (223 mg, 1.62 mmol) in DMF (10 mL) at 0° C. was added methyl iodide (83 mg, 0.59 mmol). The reaction mixture was stirred at room temperature for 10 h. The mixture was poured into ice water and the solid that precipitated was filtered and washed with methyl tert-butyl ether to afford 4-(2-(3-(3-((1H-indol-3-yl)methyl)-2-butyl-4-hydroxyphenyl)ureido)ethyl)-1,1-dimethylpiperazin-1-ium chloride (150 mg, 58%) as a white solid. $^1$H NMR (400 MHz, DMSO) δ: 0.747-0.783 (t, 3H), 1.187-1.1.223 (m, 2H), 1.282-1.339 (m, 2H), 2.484-2.386 (m, 4H), 2.763 (m, 4H), 3.166-3.114 (m, 8H), 3.444 (s, 4H), 3.848 (s, 2H), 6.651-6.619 (m, 2H), 6.744-6.732 (d, J=4.8 Hz, 1H), 6.908-6.870 (m, 1H), 7.007-6.968 (m, 2H), 7.269-7.249 (d, J=8.0 Hz, 1H), 7.548-7.528 (d, J=8.0 Hz, 1H), 9.031 (s, 1H), 9.141 (s, 1H), 10.71 (s, 1H).

The following compounds may be prepared using methods analogous to those described above in the general schemes and examples.

| Example | Chemical Structure and Name |
|---|---|
| 8 | 1-(3-((1H-indol-3-yl)methyl)-5-butylphenyl)-3-(2-(piperidin-4-yl)ethyl)urea |
| 9 | 1-(3-((1H-indol-2-yl)methoxy)-5-propoxyphenyl)-3-(2-(piperazin-1-yl)ethyl)urea |
| 10 | 1-(3-((1H-indol-2-yl)methoxy)-5-propoxyphenyl)-3-(2-(piperidin-4-yl)ethyl)urea |
| 11 | 1-(3-((1H-benzo[d]imidazol-2-yl)methyl)-5-butylphenyl)-3-(2-(4-methylpiperazin-1-yl)ethyl)urea |
| 12 | 1-(3-((1H-imidazo[4,5-b]pyrazin-2-yl)methyl)-5-butylphenyl)-3-(2-(4-methylpiperazin-1-yl)ethyl)urea |
| 13 | 1-(3-((1H-indol-3-yl)methyl)-5-isopropoxyphenyl)-3-(2-(4-methylpiperazin-1-yl)ethyl)urea |

| Example | Chemical Structure and Name |
|---------|------------------------------|
| 14 | 1-(3-((1H-indol-3-yl)methyl)-5-cyclopropoxyphenyl)-3-(2-(4-methylpiperazin-1-yl)ethyl)urea |
| 15 | 1-(3-((1H-indol-3-yl)methyl)-5-(cyclopentyloxy)phenyl)-3-(2-(4-methylpiperazin-1-yl)ethyl)urea |
| 16 | 1-(3-((1H-indol-3-yl)methyl)-5-(cyclohexyloxy)phenyl)-3-(2-(4-methylpiperazin-1-yl)ethyl)urea |
| 17 | 1-(3-((1H-indol-3-yl)methyl)-5-methoxyphenyl)-3-(2-(4-methylpiperazin-1-yl)ethyl)urea |
| 18 | 3-((1H-indol-3-yl)methoxy)-5-butylphenyl (2-(piperazin-1-yl)ethyl)carbamate |
| 19 | O-(3-((5H-pyrrolo[2,3-b]pyrazin-7-yl)methoxy)-5-propylphenyl) (2-(1H-pyrrol-2-yl)ethyl)carbamothioate |
| 20 | 1-(3-((1H-indol-3-yl)methoxy)-5-butylphenyl)-3-(2-(4-methylpiperazin-1-yl)ethyl)urea |
| 21 | 1-(3-(2-(1H-indol-3-yl)ethyl)-5-isopropylphenyl)-3-(2-(4-methylpiperazin-1-yl)ethyl)thiourea |
| 22 | 2-(4-methylpiperazin-1-yl)ethyl (3-(2-(1H-indol-3-yl)ethyl)-5-isopropylphenyl)carbamate |
| 23 | 1-(4-((1H-indol-3-yl)methyl)-3-butyl-5-methoxyphenyl)-3-(2-(4-methylpiperazin-1-yl)ethyl)urea |
| 24 | 1-(4-((1H-indol-3-yl)methyl)-3-butyl-5-(trifluoromethoxy)phenyl)-3-(2-(4-methylpiperazin-1-yl)ethyl)urea |
| 25 | 3-(3-(4-((1H-indol-3-yl)methyl)-3-ethylphenyl)ureido)propanimidamide |

| Example | Chemical Structure and Name |
|---|---|
| 26 | 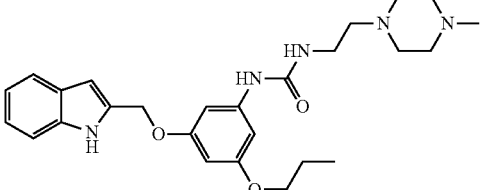<br>1-(3-((1H-indol-2-yl)methoxy)-5-propoxyphenyl)-3-(2-(4-methylpiperazin-1-yl)ethyl)urea |
| 27 | 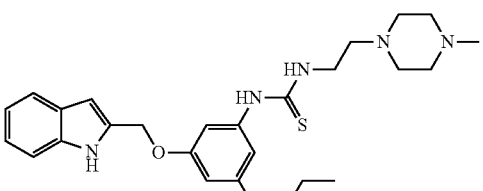<br>1-(3-((1H-indol-2-yl)methoxy)-5-propoxyphenyl)-3-(2-(4-methylpiperazin-1-yl)ethyl)thiourea |
| 28 | 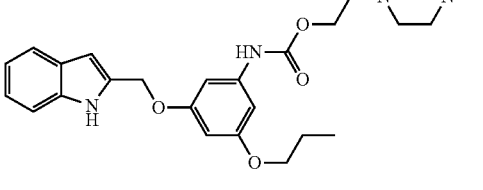<br>2-(4-methylpiperazin-1-yl)ethyl (3-((1H-indol-2-yl)methoxy)-5-propoxyphenyl)carbamate |

Example 26

In vitro cell-free and cell-based assays

Cell-Free Assay.

Recombinant α-synuclein (10 μM) are incubated at 37° C. for 16 h and then at 56° C. for 6 h with test compound. Control experiments are performed with inactive compounds that do not recognize α-synuclein, with β- and γ-synuclein and a mutant α-synuclein molecule. After incubation, the mixture is run on a SDS-PAGE gel, followed by immunoblot testing with α-synuclein antibodies. Example 2 is capable of inhibiting the aggregation of α-synuclein into oligomers in a concentration-dependent manner (FIG. 1).

Cell-Based Assay.

Figure 2:
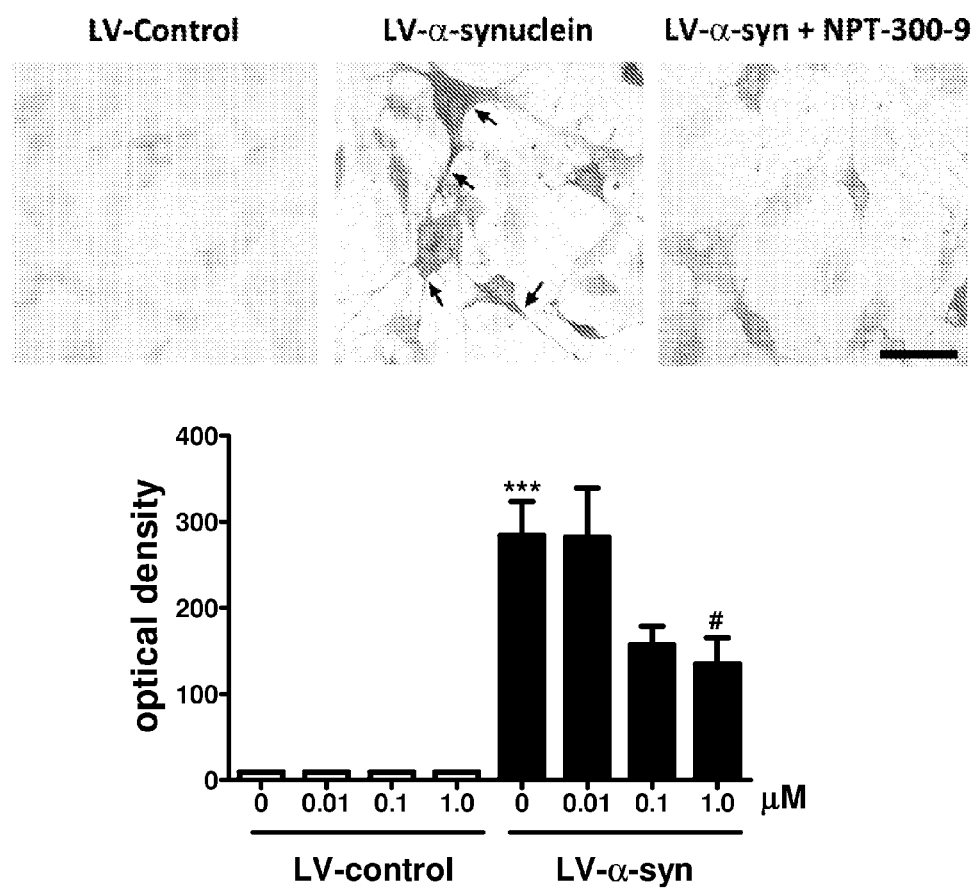
FIG. 2 shows the effects of Example 2 on synuclein accumulation and propagation in neuronal cell lines.

A neuronal cell line infected with lentivirus (LV) expressing α-synuclein (wild type) or empty vector (control) is exposed to test compounds at 0, 0.1, 1 and 10 μM for 24 h. Cells are analyzed for α-synuclein aggregation by immunoblot and confocal microscopy. By immunoblot, compared to controls, neuronal cells infected LV-α-synuclein display high levels of expression of SYN monomer (14 kDa) as well as oligomers consistent with dimers, trimers, and tetramers in the soluble and insoluble fractions. After treatment with Example 2, there was a 50-60% reduction in the levels of aggregates in the various fractions. Treatment with vehicle or with a control inactive compound had no effects in the levels of α-synuclein. In similar manner, by confocal microscopy, compared to LV-empty vector control, neuronal cells infected with LV-α-synuclein showed high levels of α-synuclein accumulation (similar to what is observed in the brains of SYN tg mice and patients with PD) (FIG. 2). After treatment with Example 2, there was a 60-65% reduction in the level of aggregates in the neuronal cell bodies and neurites (FIG. 2). Treatment with vehicle or with a control inactive compound had no effects in the levels of α-synuclein.

Figure 3:
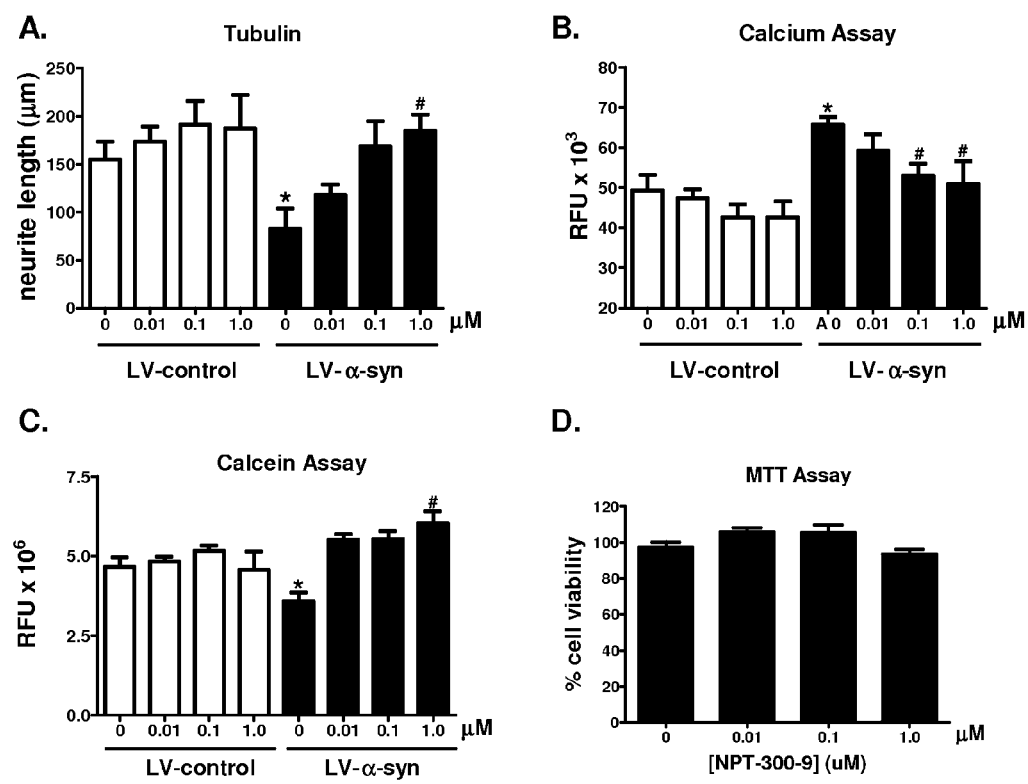
FIGS. 3A-D illustrate the effects of Example 2 in cell base tubulin (neurite length), calcium calcein and MTT assays.

Neuronal cells expressing high levels of α-synuclein displayed reduced neurite outgrowth when analyzed with an antibody against Tubulin III. Example 2 treatment (0.1 and 1.0 μM) ameliorated the deleterious effects on neurite extension and improved cellular morphology (FIG. 3A). Treatment with vehicle or with a control inactive compound had no protective effects.

Next, to ascertain the effects on neuronal activity, cells were infected with LV-α-synuclein for 24 h, treated with Example 2 at 0, 0.01, 0.1 and 1 μM for 24 h in serum free media, loaded with Fluo-4 or calcein, and analyzed by FLIPR assay to determine $Ca^{2+}$ and calcein levels. Compared to LV-empty vector control, neuronal cells infected with LV-α-synuclein showed 25-30% higher levels of $Ca^{2+}$ (FIG. 3B). Treatment with Example 2, in a concentration-dependent manner, restored concentrations of $Ca^{2+}$ to those in cells not infected with LV-α-synuclein (FIG. 3B). Treatment with vehicle or with a control inactive compound had no effect on $Ca^{2+}$ levels. Compared to LV-empty vector control, neuronal cells infected with LV-α-synuclein showed a 50% decrease in calcein retention in the cytoplasm (FIG. 3C). Treatment with Example 2, in a concentration-dependent manner, reversed the effect of α-synuclein on levels of calcein (FIG. 3C). Treatment with vehicle or with a control inactive compound was unable to re-establish calcein levels. Finally, to examine the effects Example 2 on neuronal survival, an MTT cell viability assay was performed. This study showed no toxic effects of the Example 2 at doses ranging from 0.1-10 μM, although mild toxicity was observed at 10 μM (FIG. 3D). All cell free and cell based assays were repeated at least 3 times and experiments were performed blinded to sample identity.

Data for compounds tested in the calcein assay of membrane integrity are presented in the following table:

| Ex. | Percent reversal of α-Syn mediated disruption of cell integrity (0.01 μM test compound) |
|---|---|
| 1 | 26.8 |
| 2 | 34.1 |
| 3 | 18.9 |
| 4 | 25.9 |
| 5 | 89.5 |
| 6 | 37.5 |
| 7 | 31.6 |

Example 27

In Vivo Assay

In vivo efficacy of test compounds is assessed in α-synuclein transgenic (Tg) mice. Mice are analyzed behaviorally, neuropathologically, and biochemically for α-synuclein aggregation and neurodegeneration. Blood and CSF are analyzed for levels of α-synuclein and test compound by mass spectrometry and NMR. A Tg mouse model of PD is used that overexpresses wild-type human α-synuclein under the Thy1 promoter in a mixed C57B16/DBA background (Rockenstein et al., 2002) (referred to as Line 61 tg mice). This Tg mouse develops progressive PD-like motor deficits and neuropathological indices (including alpha-synuclein aggregates and decreases in synaptic markers) starting at 3 months of age (Fleming et al., 2004). Accordingly, treatments begin in animals at 3 months of age and motor behaviors (locomotor activity and round beam performance test, as well as neuropathological and biochemically measures for α-synuclein aggregation and neurodegeneration) are assessed after 3 months of treatment at 6 months of age.

Compound administration: Test compounds are dissolved in a vehicle solution and administered at a volume of 0.1 cc per 10 grams of body weight. Animals receive a Monday-Friday daily intraperitoneal injection of vehicle or 10 mg/kg of test compound for 90 days. Behavioral assessments are conducted starting on or about day 80 of treatment.

Locomotor Activity Apparatus and testing procedure: Locomotor activity data are collected over four consecutive days using a Kinder SmartFrame Cage Rack Station activity monitor system (Kinder Scientific, Poway, Calif.). The locomotor activity testing regimen consists of four sessions (15 min ea) on four consecutive days. On each test day, each individual animal is placed into the test chamber and then data collection begins immediately. Data are processed and imported into MS Excel for subsequent analysis and graphing using GraphPad Prism (GraphPad Software, Inc., La Jolla, Calif.). Dependent measures for spontaneous locomotor activity analyzed for each animal include investigatory rearings, total distance travelled, % of time spent in periphery, % of time spent in center, and thigmotaxis. Group means are derived for each measure and analyzed by a 2-way ANOVA with genotype and treatment group as between-subjects factors. In the event of main effects or interactions, post hoc comparisons are made using Bonferroni's multiple comparisons test. The criterion for statistical significance is $p<0.05$.

Round Beam Apparatus & testing procedure: Round beam data are collected using a custom built apparatus consisting of removable 2 Delrin® acetel plastic rods (3 and 1 cm diameter) on a smooth acrylic frame elevated 17.5 to 22.5 cm above a testing bench. Each animal is tested consecutively for three trials on each 1 meter beam A (3 cm) and D (1 cm) with a brief break between each trial. Using a manual counter, each obvious foot slip past the marked line is counted by the experimenter. In addition, forward distance travelled (assessed using marked 10 cm sections on side of beam and then assigned a score) and the latency to fall (60 sec max.) for each trial is recorded for each animal. The trial ends when animal falls off the beam, reaches the maximum allowed time (60 seconds), or traverses the full distance. Raw data are recorded by hand and then entered into MS Excel for subsequent analysis and graphing using GraphPad Prism (GraphPad Software, Inc., La Jolla, Calif.). The dependent measures for performance on each diameter beam include: # of foot slips, forward distance travelled, and latency to fall. These measures are determined for each animal and presented as the mean±the standard error of the mean (SEM). Group means are determined for each measure and analyzed by a 2-way ANOVA with genotype and treatment group as between-subjects factors. In the event of main effects or interactions, post hoc comparisons are made using Bonferonni's multiple comparisons test. The criterion for statistical significance is $p<0.05$.

Neuropathology: At the completion of behavioral assessments and treatment, tissue collection, processing, and imaging methods are conducted as described previously (Masliah et al., 2000). Briefly, brains and peripheral tissues are removed and divided sagitally. The right hemibrain is post-fixed in phosphate-buffered 4% PFA (pH 7.4) at 4° C. for 48 h for neuropathological analysis, while the left hemibrain is snap-frozen and stored at −70° C. for subsequent RNA and protein analysis. Drop fixed hemibrains are then serially sectioned into 40 μM thick coronal sections using a vibratome. Sections are free-floated and incubated overnight at 4° C. with primary antibodies. To confirm the specificity of primary antibodies, control experiments are performed in which sections are incubated overnight in the absence of primary antibody (deleted), preimmune serum, or primary antibody preadsorbed for 48 h with 20-fold excess of the corresponding peptide. Immunolabeling studies of alpha-synuclein are conducted using polyclonal rabbit anti-alpha-synuclein antibodies (1:1000; Millipore, Temecula, Calif.) with studies of oligomers conducted following proteinase K digestion. Immunolabeling studies of neurodegeneration-relevant markers utilize antibodies (Millipore, Temecula, Calif.) against NeuN (1:1000, ABN78), MAP2 (1:40, AB5622), synaptophysin (1:100, MAB5258) and GFAP (1:500, AB5804) antibodies. Imaging and analysis is performed on blindcoded sections from tg and non-tg mice, as described previously by Masliah and colleagues (Masliah et al., 2000).

Ex vivo Western blot protein analysis: Processing of the cytosolic (soluble) and membrane (insoluble) fractions of mouse brain homogenates is performed as previously described (Hashimoto et al., 2001) for SDS-PAGE analysis. Briefly, for each fraction, 20 μg is loaded per lane using 4-12% Bis-Tris gels (Invitrogen, Carlsbad, Calif.). Electrophoresis onto PDGF membranes (Millipore, Temecula, Calif.) is followed by: (1) blocking, (2) incubation with primary antibodies; (3) incubation with secondary antibodies; (4) ECL visualization (PerkinElmer, Wellseley, Mass.); (4) imaging and analysis using a VersaDoc gel imaging system (Bio-Rad, Hercules, Calif.) with graphing and statistical analyses performed using GraphPad Prism (GraphPad Software, Inc., La Jolla, Calif.).

REFERENCES FOR BIOLOGICAL PROCEDURES

1) Fleming S M, Salcedo J, Fernagut P O, Rockenstein E, Masliah E, Levine M S, Chesselet M F (2004) Early and progressive sensorimotor anomalies in mice overexpressing wild-type human alpha-synuclein. J Neurosci., 24(42):9434-40.
2) Hashimoto M, Rockenstein E, Mante M, Mallory M, Masliah E (2001) beta-Synuclein inhibits alpha-synuclein aggregation: a possible role as an anti-parkinsonian factor. Neuron, 32(2):213-23.
3) Masliah E, Rockenstein E, Veinbergs I, Mallory M, Hashimoto M, Takeda A, Sagara, Sisk A, Mucke L (2000) Dopaminergic loss and inclusion body formation in alpha-synuclein mice: implications for neurodegenerative disorders. Science 287:1265-1269.
4) Rockenstein E, Mallory M, Hashimoto M, Song D, Shults C W, Lang I, Masliah E (2002) Differential neuropathological alterations in transgenic mice expressing alpha-synuclein from the platelet-derived growth factor and Thy-1 promoters. J Neurosci Res., 68(5):568-78.

The invention claimed is:
1. A compound of Formula I:

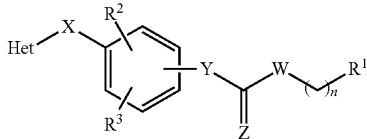

wherein
Het is 1H-indolyl, 1H-benzimidazolyl, 5H-pyrrolo[2,3-b]pyrazinyl, or 1H-imidazo[4,5-b]pyrazinyl, each unsubstituted or substituted with one or more $R^a$ substituents;
wherein each $R^a$ is independently hydroxyl, halo, amino, cyano, nitro, $C_{1-4}$alkyl, haloalkyl, $C_{1-4}$alkoxy, or halo-$C_{1-4}$alkoxy;
X is —$CH_2$—$R^z$—, wherein $R^z$ is absent, —$CH_2$—, —O—, —S—, or —NH—;
one of W and Y is NH and the other is O or NH;
Z is O or S;
$R^1$ is —$NR^bR^c$; guanidino; a monocyclic heteroaryl in which at least one ring atom is a N, and said heteroaryl is unsubstituted or is substituted with one or more $R^d$ substituents; or a monocyclic heterocycloalkyl, in which at least one ring atom is a N, and said heterocycloalkyl is unsubstituted or is substituted with one or more $R^e$ substituents;
wherein $R^b$ and $R^c$ are each independently H or $C_{1-4}$alkyl;
each $R^d$ is independently hydroxyl, halo, amino, cyano, nitro, $C_{1-4}$alkyl, haloalkyl, $C_{1-4}$alkoxy, or halo-$C_{1-4}$alkoxy; and
each $R^e$ is independently hydroxyl, halo, amino, cyano, nitro, $C_{1-4}$alkyl, haloalkyl, $C_{1-4}$alkoxy, halo-$C_{1-4}$alkoxy, —$C(O)C_{1-4}$alkyl, or —$CO_2C_{1-4}$alkyl;
n is 0, 1, 2, 3, or 4;
$R^2$ is absent or is hydroxyl, methoxy, or trifluoromethoxy; and
$R^3$ is $C_{1-6}$alkyl, $C_{1-6}$alkoxy, or $C_{3-8}$cycloalkoxy, wherein said cycloalkoxy is unsubstituted or substituted with one or more substituents selected from the group consisting of hydroxyl, halo, amino, cyano, nitro, $C_{1-4}$alkyl, haloalkyl, $C_{1-4}$alkoxy, and halo-$C_{1-4}$alkoxy;
or a pharmaceutically acceptable salt thereof.
2. The compound of claim 1, wherein Het is 1H-benzimidazolyl, 5H-pyrrolo[2,3-b]pyrazinyl, or 1H-imidazo[4,5-b]pyrazinyl.
3. The compound of claim 1, wherein Het is 1H-indolyl.
4. The compound of claim 1, wherein X is —$CH_2$—, —$CH_2CH_2$—, —$CH_2O$—, or —$CH_2NH$—.
5. The compound of claim 1, wherein X is —$CH_2$—, —$CH_2CH_2$—, or —$CH_2O$—.
6. The compound of claim 1, wherein W is O and Y is NH.
7. The compound of claim 1, wherein W is NH and Y is O.
8. The compound of claim 1, wherein W and Y are both NH.
9. The compound of claim 1, wherein Z is O.
10. The compound of claim 1, wherein $R^1$ is amino, methylamino, dimethylamino, or guanidino, or is a pyrrolyl, imidazolyl, pyrazolyl, pyridinyl, pyrimidinyl, pyrazinyl, pyridazinyl, oxazolyl, thiazolyl, isoxazolyl, isothiazolyl, triazolyl, or tetrazolyl, each unsubstituted or substituted with one or two $R^d$ substituents; or a pyrrolidinyl, piperidinyl, piperazinyl, azepanyl, morpholinyl, thiomorpholinyl, oxo-thiomorpholinyl, or dioxo-thiomorpholinyl, each unsubstituted or substituted with one or two $R^e$ substituents.
11. The compound of claim 1, wherein $R^1$ is amino or guanidino; or a pyrrolyl, imidazolyl, piperidinyl, or piperazinyl, each unsubstituted or substituted with one or two $C_{1-4}$alkyl groups.
12. The compound of claim 1, wherein n is 2.
13. The compound of claim 1, wherein $R^2$ is absent or is OH.
14. The compound of claim 1, wherein $R^3$ is methyl, ethyl, propyl, isopropyl, butyl, isobutyl, sec-butyl, tert-butyl, pentyl, methoxy, ethoxy, propoxy, isopropoxy, butoxy, cyclopropyloxy, cyclobutyloxy, cyclopentyloxy, or cyclohexyloxy.
15. The compound of claim 1, wherein $R^3$ is ethyl, propyl, isopropyl, butyl, propoxy, isopropoxy, cyclopropyloxy, cyclopentyloxy, or cyclohexyloxy.
16. A compound of Formula II:

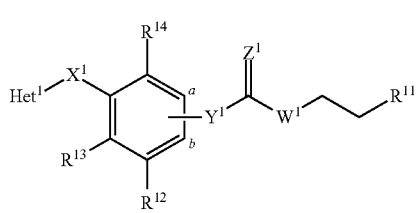

wherein
$Het^1$ is 1H-indolyl, 1H-benzimidazolyl, 5H-pyrrolo[2,3-b]pyrazinyl, or 1H-imidazo[4,5-b]pyrazinyl;
$X^1$ is —$(CH_2)_{1-2}$— or —$CH_2O$—;
one of $W^1$ and $Y^1$ is NH and the other is O or NH;
$Y^1$ is attached to the phenyl at the "a" or "b" position;
$Z^1$ is O or S;
$R^{11}$ is amino; a monocyclic heteroaryl in which at least one ring atom is a N; or a monocyclic heterocycloalkyl in which at least one ring atom is a N, and said heterocycloalkyl is unsubstituted or is substituted with one or two $C_{1-4}$alkyl groups;
when $Y^1$ is attached at the "a" position of the phenyl ring,
$R^{12}$ is $C_{2-4}$alkyl, $C_{1-3}$alkoxy, or $C_{3-7}$cycloalkoxy;
$R^{13}$ is H or hydroxy; and
$R^{14}$ is H;
and when $Y^1$ is attached at the "b" position of the phenyl ring,
$R^{12}$ is H;
$R^{13}$ is $C_{2-4}$alkyl; and
$R^{14}$ is H or hydroxyl;
or a pharmaceutically acceptable salt thereof.
17. A compound selected from the group consisting of:
3-((1H-indol-3-yl)methoxy)-5-butylphenyl (2-(4-methylpiperazin-1-yl)ethyl)carbamate;
1-(4-((1H-indol-3-yl)methyl)-3-butyl-5-hydroxyphenyl)-3-(2-(4-methylpiperazin-1-yl)ethyl)urea;
1-(4-((1H-indol-3-yl)methyl)-3-ethylphenyl)-3-(2-(4-methylpiperazin-1-yl)ethyl)urea;
1-(4-((1H-indol-3-yl)methyl)-3-ethylphenyl)-3-(2-aminoethyl)urea;
1-(4-((1H-indol-3-yl)methyl)-3-ethylphenyl)-3-(2-(piperazin-1-yl)ethyl)urea;
1-(2-(1H-imidazol-5-yl)ethyl)-3-(4-((1H-indol-3-yl)methyl)-3-ethylphenyl)urea;

4-(2-(3-(4-(((1H-indol-3-yl)methyl)-3-butyl-5-hydroxyphenyl)ureido)ethyl)-1,1-dimethylpiperazin-1-ium iodide;
1-(3-((1H-indol-3-yl)methyl)-5-butylphenyl)-3-(2-(piperidin-4-yl)ethyl)urea;
1-(3-((1H-indol-3-yl)methoxy)-5-propoxyphenyl)-3-(2-(piperazin-1-yl)ethyl)urea;
1-(3-((1H-indol-2-yl)methoxy)-5-propoxyphenyl)-3-(2-(piperazin-1-yl)ethyl)urea;
1-(3-((1H-indol-3-yl)methoxy)-5-propoxyphenyl)-3-(2-(piperidin-4-yl)ethyl)urea;
1-(3-((1H-indol-2-yl)methoxy)-5-propoxyphenyl)-3-(2-(piperidin-4-yl)ethyl)urea;
1-(3-((1H-benzo[d]imidazol-2-yl)methyl)-5-butylphenyl)-3-(2-(4-methylpiperazin-1-yl)ethyl)urea;
1-(3-((1H-imidazo[4,5-b]pyrazin-2-yl)methyl)-5-butylphenyl)-3-(2-(4-methylpiperazin-1-yl)ethyl)urea;
1-(3-((1H-indol-3-yl)methyl)-5-isopropoxyphenyl)-3-(2-(4-methylpiperazin-1-yl)ethyl)urea;
1-(3-((1H-indol-3-yl)methyl)-5-cyclopropoxyphenyl)-3-(2-(4-methylpiperazin-1-yl)ethyl)urea;
1-(3-((1H-indol-3-yl)methyl)-5-(cyclopentyloxy)phenyl)-3-(2-(4-methylpiperazin-1-yl)ethyl)urea;
1-(3-((1H-indol-3-yl)methyl)-5-(cyclohexyloxy)phenyl)-3-(2-(4-methylpiperazin-1-yl)ethyl)urea;
1-(3-((1H-indol-3-yl)methyl)-5-methoxyphenyl)-3-(2-(4-methylpiperazin-1-yl)ethyl)urea;
3-((1H-indol-3-yl)methoxy)-5-butylphenyl (2-(piperazin-1-yl)ethyl)carbamate;
O(3-((5H-pyrrolo[2,3-b]pyrazin-7-yl)methoxy)-5-propylphenyl) (2-(1H-pyrrol-2-yl)ethyl)carbamothioate;
1-(3-((1H-indol-3-yl)methoxy)-5-butylphenyl)-3-(2-(4-methylpiperazin-1-yl)ethyl)urea;
1-(3-(2-(1H-indol-3-yl)ethyl)-5-isopropylphenyl)-3-(2-(4-methylpiperazin-1-yl)ethyl)thiourea;
2-(4-methylpiperazin-1-yl)ethyl (3-(2-(1H-indol-3-yl)ethyl)-5-isopropylphenyl)carbamate;
1-(4-((1H-indol-3-yl)methyl)-3-butyl-5-methoxyphenyl)-3-(2-(4-methylpiperazin-1-yl)ethyl)urea;
1-(4-((1H-indol-3-yl)methyl)-3-butyl-5-(trifluoromethoxy)phenyl)-3-(2-(4-methylpiperazin-1-yl)ethyl)urea;
3-(3-(4-((1H-indol-3-yl)methyl)-3-ethylphenyl)ureido)propanimidamide;
1-(3-((1H-indol-2-yl)methoxy)-5-propoxyphenyl)-3-(2-(4-methylpiperazin-1-yl)ethyl)urea;
1-(3-((1H-indol-2-yl)methoxy)-5-propoxyphenyl)-3-(2-(4-methylpiperazin-1-yl)ethyl)thiourea; and
2-(4-methylpiperazin-1-yl)ethyl (3-((1H-indol-2-yl)methoxy)-5-propoxyphenyl)carbamate;
and pharmaceutically acceptable salts thereof.

18. A pharmaceutical composition comprising (a) at least one compound of Formula I as in claim 1, or a pharmaceutically acceptable salt thereof, and (b) a pharmaceutically acceptable excipient.

\* \* \* \* \*